United States Patent [19]

Beck et al.

[11] Patent Number: 4,931,083

[45] Date of Patent: Jun. 5, 1990

[54] PLANT GROWTH REGULATING TRIAZOLES

[75] Inventors: James R. Beck, Indianapolis, Ind.; Richard K. Mann, Mahomet, Ill.

[73] Assignee: Eli Lilly and Company, Indianapolis, Ind.

[21] Appl. No.: 916,987

[22] Filed: Oct. 9, 1986

Related U.S. Application Data

[63] Continuation-in-part of Ser. No. 861,944, May 12, 1986, abandoned, which is a continuation-in-part of Ser. No. 797,304, Nov. 12, 1985, abandoned.

[51] Int. Cl.$^5$ .............. A01N 43/653; C07D 249/12; C07D 401/12
[52] U.S. Cl. ............................ 71/92; 71/88; 71/94; 71/95; 544/132; 546/210; 548/264.4
[58] Field of Search ............. 548/265; 546/210; 544/132; 71/92, 94, 95, 88

[56] References Cited

U.S. PATENT DOCUMENTS

| | | | |
|---|---|---|---|
| 3,701,784 | 10/1972 | Seidel et al. | |
| 4,115,100 | 9/1978 | Schurter et al. | 71/94 |
| 4,180,395 | 12/1979 | Johnston et al. | 71/94 |
| 4,399,285 | 8/1983 | Forster et al. | 546/210 |
| 4,408,055 | 10/1983 | Forster et al. | 548/125 |
| 4,428,766 | 1/1984 | Hamprecht et al. | 71/91 |

FOREIGN PATENT DOCUMENTS

| | | | |
|---|---|---|---|
| 18497 | 3/1980 | European Pat. Off. | 71/91 |
| 39811 | 4/1981 | European Pat. Off. | 71/91 |
| 109751 | 5/1984 | European Pat. Off. | 546/290 |
| 0155486 | 9/1985 | European Pat. Off. | 514/359 |
| 0157259 | 9/1985 | European Pat. Off. | 514/359 |
| 1943915 | 8/1969 | Fed. Rep. of Germany | 514/359 |
| 2412564 | 3/1974 | Fed. Rep. of Germany | 548/265 |
| 2546845 | 10/1975 | Fed. Rep. of Germany | 546/153 |
| 55-100306 | 1/1979 | Japan | 596/290 |
| 55-100307 | 1/1979 | Japan | 546/290 |
| 59088470 | 11/1982 | Japan | 548/265 |
| 2056971 | 3/1981 | United Kingdom | 71/92 |

*Primary Examiner*—Robert T. Bond
*Attorney, Agent, or Firm*—Donald R. Stuart; Leroy Whitaker; Joseph A. Jones

[57] ABSTRACT

A series of triazole compounds having a carboxyalkoxy(thio) group, or a derivative thereof, are useful for regulating the growth of plants, particularly the growth of soybeans.

26 Claims, No Drawings

PLANT GROWTH REGULATING TRIAZOLES

CROSS-REFERENCE

This application is a continuation-in-part of copending application Ser. No. 861,944, filed on May 12, 1986, which is a continuation-in-part of copending application Ser. No. 797,304, filed on Nov. 12, 1985, both now abandoned.

BACKGROUND OF THE INVENTION

Workers in the field of agricultural chemistry and plant physiology have known for some time that certain chemicals are able to control plant behavior in beneficial ways. For example, compounds have been found which modify plant growth, enhance the yield of crops, improve the quality of crops, or improve mechanical harvesting operations by altering the growth habit of plants. Compounds which are applied to a plant to alter its processes or structure in a beneficial way are called plant growth regulators. Some instances of goals of plant growth regulation are the slowing of growth of turf to decrease the frequency of mowing, the shortening of grain stems to decrease lodging, causing ornamental plants to be more compact, increasing flowering of fruit-bearing crops, increasing fruit set of tomatoes, and reducing the size of crop plants so that they can be planted more densely.

SUMMARY OF THE INVENTION

The present invention provides triazole compounds of the formula

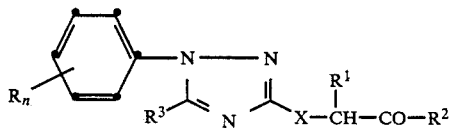

wherein
n is 0, 1 or 2;
X is —O— or —S—;
the R groups independently are halo, trifluoromethyl, trifluoromethoxy, difluoromethoxy, pentafluoroethoxy, 1,1,2,2-tetrafluoroethoxy, $C_1$-$C_3$ alkyl or $C_1$-$C_3$ alkoxy;
$R^1$ is $C_1$-$C_4$ primary or secondary alkyl;
$R^2$ is hydroxy, $C_1$-$C_4$ alkoxy, benzyloxy, phenoxy, —N($R^4$)($R^5$) or a moiety forming a phytologically-acceptable salt;
$R^3$ is hydrogen or $C_1$-$C_4$ primary or secondary alkyl;
$R^4$ and $R^5$ independently are hydrogen, $C_3$-$C_6$ cycloalkyl or $C_1$-$C_3$ alkyl, or $R^4$ and $R^5$ combine with the nitrogen atom to which they are attached to form morpholino, pyrrolidino or piperidino.

The invention also provides agricultural compositions comprising the above compounds and a phytologically-acceptable diluent, and further provides a method of regulating the growth of plants which comprises applying an effective amount of a compound of the above formula to the plant to be regulated at a time not later than the late reproductive growth stage.

DESCRIPTION OF THE PREFERRED EMBODIMENTS

Compounds

Throughout the present document, all temperatures will be expressed in degrees Celsius. All expressions of concentration, proportion and the like will refer to weight units unless otherwise stated.

In the above formula, the general chemical terms have their usual meanings. For example, the terms $C_1$-$C_3$ alkyl and $C_1$-$C_3$ alkoxy include the groups methyl, ethyl, propyl, and isopropyl, which may be linked through an oxygen atom to form the alkoxy groups. The term $C_1$-$C_4$ alkoxy includes the above alkoxy groups, and also includes butoxy, 1-methylpropoxy, 2-methylpropoxy and t-butoxy. The term $C_1$-$C_4$ primary or secondary alkyl includes methyl, ethyl, propyl, isopropyl, butyl, 1-methylpropyl and 2-methylpropyl. The term $C_3$-$C_6$ cycloalkyl includes such groups as cyclopropyl, cyclobutyl and cyclohexyl.

The term halo includes fluoro, chloro, bromo and iodo.

The above formula describes the compounds of the present invention, but the following group of compounds are specifically mentioned to assure that the invention is easily understood.

3-(1-carboxyethoxy)-1-(2-fluorophenyl)-1,2,4-1H-triazole 3-(1-carboxypropoxy)-1-(4-chlorophenyl)-1,2,4-1H-triazole, sodium salt 1-(3-bromophenyl)-3-(1-methoxycarbonylbutylthio)-5-methyl-1,2,4-1H-triazole 3-(1-ethoxycarbonyl-2-methylpropoxy)-1-(4-iodophenyl)-1,2,4-1H-triazole 5-ethyl-3-(1-propoxycarbonylpentylthio)-1-(3-trifluoromethylphenyl)-1,2,4-1H-triazole 3-(1-isopropoxycarbonyl-2-methylbutoxy)-5-methyl-1-(3-methylphenyl)-1,2,4-1H-triazole 3-(1-butoxycarbonyl-3-methylbutoxy)-1-(2-ethylphenyl)-5-methyl-1,2,4-1H-triazole 3-(1-isobutoxycarbonylethoxy)-5-isopropyl-1-(4-isopropylphenyl)-1,2,4-1H-triazole 3-(1-s-butoxycarbonylethoxy)-1-(4-methoxyphenyl)-5-methyl-1,2,4-1H-triazole 3-(1-t-butoxycarbonylpropoxy)-1-(3-ethoxyphenyl)-5-propyl-1,2,4-1H-triazole 3-(1-benzyloxycarbonylethoxy)-1-(2-isopropoxyphenyl)-5-methyl-1,2,4-1H-triazole 5-butyl-3-(1-carboxyethylthio)-1-(3,5-difluorophenyl)-1,2,4-1H-triazole, potassium salt 1-(2,4-dibromophenyl)-5-methyl-3-(1-phenoxycarbonylbutoxy)-1,2,4-1H-triazole 3-(1-aminocarbonylethoxy)-1-[3,5-bis(trifluoromethyl)phenyl]-1,2,4-1H-triazole 3-(1-methylaminocarbonylethoxy)-1-(2,5-dimethylphenyl)-1,2,4-1H-triazole 3-(1-ethylaminocarbonylethylthio)-1-(2,6-diethylphenyl)-1,2,4-1H-triazole 5-(1-methylpropyl)-1-[3,4-bis(methoxy)phenyl]-3-(1-propylaminocarbonylpropoxy)-1,2,4-1H-triazole 3-(1-isopropylaminocarbonylethoxy)-1-[2,4bis(propoxy)phenyl]-1,2,4-1H-triazole 3-(1-ethylmethylaminocarbonyl-2-methylpropoxy)-1-(2-fluoro-4-trifluoromethylphenyl)-1,2,4-1H-triazole 1-(3-bromo-5-chlorophenyl)-5-isobutyl-3-(1-dipropylaminocarbonylethoxy)-1,2,4-1H-triazole 3-(1-ethylpropylaminocarbonylethylthio)-1-(4-fluoro-3-iodophenyl)-1,2,4-1H-triazole 1-(3-chloro-4-ethylphenyl)-3-(1-isopropylmethylaminocarbonylpentoxy)-1,2,4-1H-triazole 1-(2-bromo-4-isopropylphenyl)-3-(1-morpholinocarbonylethoxy)-1,2,4-1H-triazole 1-(2-fluoro-5-methylphenyl)-3-(1-pyrrolidinocarbonyle-
thoxy)-1,2,4-1H-triazole
1-(2-chloro-3-methoxyphenyl)-5-methyl-3-(1-
piperidinocarbonyl-2-methylbutylthio)-1,2,4-triazole
3-(1-carboxyethoxy)-1-(2-fluoro-4-isopropoxyphenyl)-
1,2,4-1H-triazole
3-(1-methoxycarbonylethoxy)-1-(4-methyl-3-tri-
fluoromethylphenyl)-1,2,4-1H-triazole
3-(1-carboxyethoxy)-1-(2-propyl-4-trifluoromethyl-
phenyl)-1,2,4-1H-triazole, triethylamine salt
1-(3-ethoxy-5-trifluoromethylphenyl)-3-(1-propoxycar-
bonyl-3-methylbutylthio)-1,2,4-1H-triazole
3-(1-aminocarbonylethoxy)-1-(4-isopropoxy-2-tri-
fluoromethylphenyl)-1,2,4-1H-triazole
1-(4-methoxy-3-methylphenyl)-5-methyl-3-(1-phenox-
ycarbonylethylthio)-1,2,4-1H-triazole
3-(1-carboxypropoxy)-1-(5-ethoxy-2-propylphenyl)-
1,2,4-1H-triazole, pyridine salt
3-(1-carboxyethoxy)-1-(4-isopropoxy-2-isopropyl-
phenyl)-1,2,4-1H-triazole
1-(4-chlorophenyl)-3-(1-cyclopropylaminocarbonyl-
propylthio)-1,2,4-1H-triazole
3-[1-(cyclobutyl)(methyl)aminocarbonylethylthio]-1-
(3-trifluoromethylphenyl)-1,2,4-1H-triazole
3-(1-cyclohexylaminocarbonylethoxy)-1-(3,5-dichloro-
phenyl)-1,2,4-triazole
3-[1-(cyclopentyl)(ethyl)aminocarbonyl-2-methyl-
propoxy]-5-methyl-1-(3,5-dimethylphenyl)-1,2,4-1H-
triazole
3-[1-bis(cyclobutyl)aminocarbonylethylthio]-1-phenyl-
1,2,4-1H-triazole
1-(4-chloro-3-methylphenyl)-3-(1-cyclo-
propylaminocarbonylpropoxy)-5-ethyl-1,2,4-1H-
triazole
3-(1-cyclohexylaminocarbonylbutylthio)-1-(3-methoxy-
phenyl)-1,2,4-1H-triazole
3-(1-carboxyethoxy)-1-(3,5-dichlorophenyl)-1,2,4-1H-
triazole, triethanolamine salt
3-(1-carboxyethoxy)-1-(3,5-dimethylphenyl)-1,2,4-
triazole
3-(1-carboxyethoxy)-1-(4-fluoro-3-difluoromethoxy-
phenyl)-1,2,4-1H-triazole
3-(1-carboxyethoxy)-1-(3-pentafluoroethoxyphenyl)-
1,2,41H-triazole, potassium salt
3-(1-cyclopropylaminocarbonylethoxy)-1-[2-chloro-4-
(1,1,2,2-tetrafluoroethoxy) phenyl]-1,2,4-1H-triazole
3-(1-carboxyethoxy)-1-[3,5-bis(trifluoromethoxy)-
phenyl]-1,2,4-1H-triazole, triethylamine salt While all of the compounds of the present invention
are useful, certain sub-classes of the compounds are
particularly preferred.

One such preferred class includes compounds of the
formula

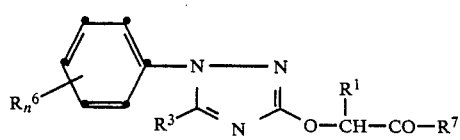

wherein
n is 0, 1 or 2;
the $R^6$ groups independently are halo, trifluoro-
methyl, $C_1$–$C_3$ alkyl or $C_1$–$C_3$ alkoxy;
$R^1$ is $C_1$–$C_4$ primary or secondary alkyl;

$R^7$ is hydroxy, $C_1$–$C_4$ alkoxy, benzyloxy, phenoxy,
—N($R^8$)($R^9$) or a moiety forming a phytologically-
acceptable salt;
$R^3$ is hydrogen or $C_1$–$C_4$ primary or secondary alkyl;
$R^8$ and $R^9$ independently are hydrogen or $C_1$–$C_3$
alkyl, or $R^8$ and $R^9$ combine with the nitrogen atom to
which they are attached to form morpholino, pyr-
rolidino or piperidino.

The following limitations set out further preferred
classes. It will be understood that the limitations can be
combined to create further preferred groups.
 1. $R^1$ is methyl;
 2. $R^3$ is hydrogen or methyl;
 3. $R^3$ is hydrogen;
 4 $R^2$ is hydroxy or a physiologically-acceptable moi-
ety forming a salt;
 5. $R^2$ is alkoxy;
 6. $R^2$ is alkoxy, benzyloxy or phenoxy;
 7. R is halo or trifluoromethyl and n is 1 or 2;
 8. R is halo and n is 1 or 2;
 9 R is trifluoromethyl and n is 1;
 10. R is chloro and n is 1 or 2;
 11. X is —O—;
 12. $R^4$ and $R^5$ are independently hydrogen or $C_1$–$C_3$
alkyl.

Synthesis

The compounds of the present invention are readily
and economically prepared by processes which are
analogous to well known synthetic steps. The processes
will be briefly discussed in general here, and the prepar-
ative examples which follow illustrate in detail the syn-
thesis of the compounds and their intermediates.

The first intermediate for the compounds is a 1-
phenylsemicarbazide, having the substituents on the
phenyl ring which will characterize the desired prod-
uct. The semicarbazide is readily obtained by reacting
the corresponding phenylhydrazine, preferably in the
form of a hydrohalide salt, with a cyanate, preferably an
alkali metal cyanate. The process can be readily carried
out in water at a moderately elevated temperature in the
range of 50°–100°, when the preferred forms of the
reactants are used. Moderate reaction times such as a
few hours are adequate to produce excellent yields.

When a compound wherein X is —S— is to be made,
the intermediate is, of course, a 1-phenylthiosemicarba-
zide, prepared from a thiocyanate.

The above step, as well as the other steps to be de-
scribed below, may be operated either to maximize
yield or to maximize throughput of the process, as may
be desirable in the circumstances. The most preferred
reaction conditions will differ, of course, depending on
which goal is desired. However, it will be found that the
synthetic steps are readily carried out to maximize ei-
ther yield or throughput, and that it is not necessary to
use large excess amounts of any reactant in order to
obtain good utilization of the other reactants.

The second intermediate in the present synthesis is a
3-hydroxy(thiono)-1-aryl-1,2,4-1H-triazole, which is
prepared by reacting the (thio)semicarbazide with an
orthoester. When the desired product has no 5-substitu-
ent ($R^3$ is hydrogen) the orthoester is an orthoformate.
Formic acid may be used instead of an orthoformate. If
the product is to have a 5-substituent, the orthoester is
chosen to provide the desired substituent. For example,
use of an orthoacetate gives a 5-methyl product; use of
an orthobutyrate gives a 5-propyl product.

Excellent results in the preparation of the hydroxy(thiono)triazole have been obtained when the orthoester was used in sufficient amount to serve as the reaction solvent, and a small amount of p-toluenesulfonic acid was used as a reaction initiator. Elevated temperatures in the range of 80°–120° are suitable. However, the step may also be carried out in an inert solvent, such as, for example, an amide or sulfoxide solvent, using only an approximately stoichiometric amount of the orthoester. Of course, the process may be operated at a temperature above the boiling point of the solvent by carrying out the step under pressure.

The hydroxy(thiono)triazoles are converted to esters of the present invention (wherein $R^2$ is alkoxy) by reacting them with an intermediate of the formula

wherein X is chloro or bromo, preferably bromo, and Alk is $C_1$–$C_4$ alkyl, most conveniently ethyl. The reaction is carried out in an inert solvent, most preferably in an amide or sulfoxide solvent, in the presence of a strong base. The preferred solvents are dimethylsulfoxide, dimethylformamide and dimethylacetamide, and the preferred strong bases are the alkali metal hydrides and alkoxides. The reaction is economically carried out at elevated temperatures in the range of about 80°–150°, under pressure if it is economically practical to do so.

When other products of the present invention are desired, the esters prepared in the step which has just been described are easily converted. It is possible to convert such an ester directly to an amide by reacting it with the appropriate substituted amine or with ammonium hydroxide. Such reactions are comparatively slow but may be used if desired. The reactions can be carried out in any convenient solvent, such as an amide, ketone, sulfoxide or the like, at ambient temperature or at a moderately elevated temperature up to about 100°.

The esters are readily hydrolyzed to the corresponding carboxylic acids. The most convenient hydrolyzing agents are strong inorganic bases such as the alkali metal hydroxides and carbonates, especially the hydroxides. Aqueous alkanols such as methanol, ethanol and the like are conventionally used for hydrolysis and are preferred. Operation at the reflux temperature of the reaction medium gives relatively quick hydrolysis to prepare the acid in high and economical yields.

The carboxylic acid may easily be converted to any desired salt, ester or amide of the present invention. The acids are esterified in the usual ways, for example, by reaction with the appropriate alcohol. Often, it is convenient to first convert the acid to an acid halide, as by reaction with thionyl chloride, thionyl bromide, phosphorus oxychloride or the like, and then to react with the alcohol. The esterification may be carried out directly, by reacting with the alcohol in the presence of an inorganic acid, especially sulfuric acid or in the presence of a coupling agent such as carbonyldiimidazole. The acid halide may be isolated, or may be formed and further reacted in the same reaction mixture. Inexpensive inert solvents such as aromatics and the like are adequate reaction solvents for the process. Alternatively, the acids may be esterified with a halide of the desired $R^2$ group, carrying out the reaction in the presence of a strong base such as an alkali metal alkoxide.

Finally, the carboxylic acids are converted to the corresponding amides by reaction with the appropriate substituted amine or with ammonium hydroxide. It is preferred to use a coupling agent, such as carbonyldiimidazole, in such a reaction step, and to carry the process out in a highly inert solvent such as an amide, of which such solvents as dimethylformamide and dimethylacetamide are preferred. The reactions go conveniently at ambient temperature in moderate periods of time.

Salts of the carboxylic acids are easily prepared in the usual manner, by simply contacting the compound with the appropriate base in an aqueous alkanol or aqueous ketone. For example, alkali metal salts are obtained by using a base such as sodium, lithium or potassium hydroxide, carbonate or bicarbonate. Amine salts are obtained by using an amine base such as triethylamine, triethanolamine, pyridine, butyldimethylamine and the like. Salts are prepared at moderate temperatures in the range of 0°–100°.

The following preparations and examples further illustrate the synthesis of the compounds of the present invention. It will be understood that the preparations and examples are illustrative, and that skilled organic chemists may find it advisable to modify the conditions of the following synthesis, in some instances, in order to prepare other compounds of the invention most efficiently.

Preparation 1

1-(2,4-dichlorophenyl)semicarbazide

A 20 g portion of 2,4-dichlorophenylhydrazine hydrochloride was added to 200 ml of water and the solution was heated to 80°. Then 6.8 g of potassium cyanate was dissolved in 75 ml of water, and that solution was added dropwise to the first solution. The mixture was stirred for 4 hours at 80°, and it was then cooled. The product was collected by filtration, dried, and recrystallized from ethanol to obtain 11.8 g of the desired intermediate.

Preparation 2

3-hydroxy-1-phenyl-1,2,4-1H-triazole

One hundred g of 1-phenylsemicarbazide was added to 500 ml of trimethyl orthoformate, and about 400 mg of p-toluenesulfonic acid was added to the mixture. It was heated on a steam bath with strong agitation for 2 hours, and was then transferred to a large flask, cooled and evaporated under vacuum. The residue was recrystallized from about 1600 ml of acetic acid to obtain 97 g of the desired intermediate, m.p. 277°–280°.

Theory: C, 59.62; H, 4.38; N, 26.07; Found: C, 59.35; H, 4.25; N, 25.86.

Preparation 3

3-hydroxy-5-methyl-1-phenyl-1,2,4-1H-triazole

Twenty-five g of 1-phenylsemicarbazide and 150 ml of trimethyl orthoacetate were combined, and 100 mg of p-toluenesulfonic acid was added. The mixture was stirred on a steam bath for 5 hours, and was then cooled and evaporated under vacuum. The residue was recrystallized from ethanol to obtain 24.6 g of the desired product.

Theory: C, 61.70; H, 5.18; N, 23.99; Found: C, 61.62; H, 5.32; N, 23.79.

Preparation 4

1-(4-chlorophenyl)thiosemicarbazide

Fifty g of 4-chlorophenylhydrazine hydrochloride and 40 g of ammonium thiocyanate were added to 250 ml of denatured ethanol and the mixture was stirred under reflux for 16 hours. It was then filtered while still hot and the filter cake was washed with about 100 ml of hot ethanol. As the filtrate cooled, the product began to crystallize, and it was collected and recrystallized from denatured ethanol to obtain 32.7 g of the desired intermediate, m.p. 200°–201°.

Theory: C, 41.69; H, 4.00; N, 20.84; Found: C, 41.66; H, 3.85; N, 20.56.

Preparation 5

1-(4-chlorophenyl)-3-thiono-1,2,4-1H-triazole

Twelve g of 1-(4-chlorophenyl)thiosemicarbazide was suspended in 60 ml of 95% formic acid, and the mixture was stirred under reflux for 24 hours. The mixture was then cooled, and the product precipitated. It was collected and washed with cold denatured ethanol, and was dried to obtain 6.1 g of the desired intermediate, m.p. 222°–224°.

Theory: C, 45.39; H, 2.86; N, 19.85; Found: C, 45.41; H, 2.60; N, 19.62.

The above preparations illustrate the synthesis of the first and second intermediates for all of the products of the present invention. Only minor adjustment of the above conditions will be found to be necessary in order to maximize the efficiency of the preparation of any intermediate.

EXAMPLE 1

3-(1-ethoxycarbonylethoxy)-1-phenyl-1,2,4-1H-triazole

Five g of the compound of Preparation 2 was dissolved in 75 ml of dimethylsulfoxide, and to it was added 1.7 g of sodium methoxide. The solution was stirred on a steam bath for 1 hour, and it was then briefly put under vacuum to remove the methanol which was formed. To it was then added 5.6 g of ethyl 2-bromopropionate, and the mixture was stirred on the steam bath overnight. It was then poured over ice-water, and the resulting solid was collected, dried and crystallized from methanol-water. The precipitate was taken up in a small amount of diethyl ether, washed with 1N aqueous sodium hydroxide and then with water, and was dried over magnesium sulfate. The solvent was removed under vacuum to obtain 600 mg of the desired product, m.p. 88°–89°.

Theory: C, 59.76; H, 5.79; N, 16.08; Found: C, 59.64; H, 5.97; N, 15.85.

EXAMPLE 2

3-(1-ethoxycarbonylethoxy)-1-(2,4-dichlorophenyl)-1,2,4-1H-triazole

Thirteen g of 3-hydroxy-1-(2,4-dichlorophenyl)-1,2,4-1H-triazole was added to a solution of sodium methoxide (prepared from 1.3 g of sodium and excess methanol) in 200 ml of dimethylsulfoxide. The solution was heated on a steam bath for 2 hours, and then 10 g of ethyl 2-bromopropionate was added and heating was continued for 1.5 hours more. The mixture was then cooled, poured over ice-water, and extracted with 200 ml of diethyl ether. The ether extract was washed with 1N hydrochloric acid, with saturated aqueous sodium bicarbonate, and finally with saturated brine, and was dried with sodium sulfate and phase separation paper. The solvent was removed under vacuum to obtain 16 g of the desired product, an oil.

Theory: C, 47.29; H, 3.97; N, 12.73; Found: C, 47.09; H, 4.06; N, 12.48.

EXAMPLE 3

3-(1-ethoxycarbonylethoxy)-1-(3-trifluoromethylphenyl)-1,2,4-1H-triazole

A 1.7 g portion of sodium was dissolved in 30 ml of methanol, and the solution was added to 150 ml of dimethylsulfoxide. To it was added 17 g of 3-hydroxy-1-(3-trifluoromethylphenyl)-1,2,4-1H-triazole, and the solution was heated on the steam bath for 90 minutes. To it was then added 13.4 g of ethyl 2-bromopropionate, and heating was continued for 90 minutes more. The mixture was then cooled and poured over ice-water. The solid was collected, dried and recrystallized from ethanol to obtain 20.5 g of the desired product, m.p. 100°–102°.

Theory: C, 51.07; H, 4.29; N, 12.76; Found: C, 50.83; H, 4.48; N, 12.83.

EXAMPLE 4

1-(2-chlorophenyl)-3-(1-ethoxycarbonylethoxy)-1,2,4-1H-triazole

The process was carried out essentially according to that of Example 2 above, starting with 1.2 g of sodium, 30 ml of methanol, 10 g of 1-(2-chlorophenyl)-3-hydroxy-1,2,4-1H-triazole and 9.3 g of ethyl 2-bromopropionate. The solvent was 100 ml of dimethylsulfoxide. The product obtained was 14 g of the desired product, an oil.

Theory: C, 52.80; H, 4.77; N, 14.21; Found: C, 52.61; H, 4.77; N, 13.98.

EXAMPLE 5

1-(3-chlorophenyl)-3-(1-ethoxycarbonylethoxy)-1,2,4-1H-triazole

A 2.2 g portion of sodium was dissolved in 75 ml of methanol and the solution was added to 100 ml of dimethylsulfoxide. To that was added 19.2 g of 1-(3-chlorophenyl)-3-hydroxy-1,2,4-1H-triazole, and the mixture was stirred on the steam bath for 4 hours. To it was then added 17.7 g of ethyl 2-bromopropionate, and heating was continued for 2 hours more. The mixture was then cooled and poured over ice-water, and the solid was collected, dried and recrystallized from ethanol and then from toluene to obtain 8.5 g of the desired product, m.p. 70°–72°.

Theory: C, 52.80; H, 4.77; N, 14.21; Found: C, 52.97; H, 4.60; N, 14.47.

EXAMPLE 6

1-(3,4-dichlorophenyl)-3-(1-ethoxycarbonylethoxy)-1,2,4-1H-triazole

The process was carried out essentially like that of Example 5, using 0.8 g of sodium, 20 ml of methanol, 100 ml of dimethylsulfoxide, 8 g of 1-(3,4-dichlorophenyl)-3-hydroxy-1,2,4-1H-triazole and 6.3 g of ethyl 2-bromopropionate. The product was 7.7 g of the desired product, m.p. 69°–71°.

Theory: C, 47.29; H, 3.97; N, 12.73; Found: C, 47.13; H, 3.87; N, 12.54.

EXAMPLE 7

3-(1-ethoxycarbonylethoxy)-5-methyl-1-phenyl-1,2,4-1H-triazole

A 3.2 g portion of sodium was dissolved in 50 ml of methanol, and the solution was added to 100 ml of dimethylsulfoxide. To it was added 24.6 g of 3-hydroxy-5-methyl-1-phenyl-1,2,4-1H-triazole, and the solution was heated on the steam bath for 2 hours, adding 100 ml of additional dimethylsulfoxide. To the solution was then added 25.4 g of ethyl 2-bromopropionate, and heating was continued for 2 hours more. The reaction mixture was then cooled, poured over ice-water, and extracted with 300 ml of chloroform. The extract was washed with water and with saturated brine, and was dried with sodium sulfate and phase separation paper. The solvent was removed under vacuum, and the product was distilled at 1.2 mm of mercury and 192° to obtain 20 g of the desired product, an oil.

Theory: C, 61.08; H, 6.22; N, 15.26; Found: C, 61.37; H, 6.34; N, 15.39.

EXAMPLE 8

3-(1-ethoxycarbonylethoxy)-1-(4-methoxyphenyl)-1,2,4-1H-triazole

A 1.3 g portion of sodium was dissolved in 30 ml of methanol, and the solution was added to 150 ml of dimethylsulfoxide. To it was added 11 g of 3-hydroxy-1-(4-methoyphenyl)-1,2,4-1H-triazole, and the solution was heated at 60° for 2 hours. To it was then added 10.4 g of ethyl 2-bromopropionate, and the mixture was heated on the steam bath for 4 hours more. It was then cooled and poured over ice-water, and the solid was collected, dried and recrystallized from ethanol-water. The impure product was purified by taking it up in 1:1 ethyl acetate:hexane and passing it through a high performance liquid chromatographic column filled with silica gel. The solvent was removed from the product-containing fractions to obtain 6.3 g of the desired product, m.p. 62°–64°.

Theory: C, 57.72; H, 5.88; N, 14.42; Found: C, 57.43; H, 5.69; N, 14.70.

EXAMPLE 9

3-(1-ethoxycarbonylbutoxy)-1-phenyl-1,2,4-1H-triazole

The synthesis was carried out substantially as shown above in Example 7, except that it was necessary to chromatograph the product as described in Example 8. The reactants were 0.7 g of sodium, 20 ml of methanol, 5 g of 3-hydroxy-1-phenyl-1,2,4-1H-triazole and 6.5 g of ethyl 2-bromopentanoate. The solvent was 80 ml of dimethylsulfoxide. Five g of the desired product, an oil, was obtained.

Theory: C, 62.27; H, 6.62; N, 14.52; Found: C, 62.04; H, 6.90; N, 14.25.

EXAMPLE 10

3-(1-ethoxycarbonylpentoxy)-1-phenyl-1,2,4-1H-triazole

The process was carried out as shown in Example 7 above, beginning with 1.4 g of sodium, 30 ml of methanol, 150 ml of dimethylsulfoxide, 10 g of 3-hydroxy-1-phenyl-1,2,4-1H-triazole and 13.8 g of ethyl 2-bromohexanoate. The product was distilled at 205° and 1 mm of mercury to obtain 5.2 g of the desired product, an oil.

Theory: C, 63.35; H, 6.98; N, 13.85; Found: C, 63.62; H, 7.14; N, 13.75.

EXAMPLE 11

3-(1-ethoxycarbonylethoxy)-1-(4-methylphenyl)-1,2,4-1H-triazole

The process was carried out as described in Example 8, starting with 1.1 g of sodium, 20 ml of methanol, 150 ml of dimethylsulfoxide, 8.5 g of 3-hydroxy-1-(4-methylphenyl)-1,2,4-1H-triazole and 8.7 g of ethyl 2-bromopropionate. A yield of 3.8 g of the desired product, m.p. 69°–71°, was obtained.

Theory: C, 61.08; H, 6.22; N, 15.27; Found: C, 60.90; H, 6.22; N, 15.11.

EXAMPLE 12

1-(4-chlorophenyl)-3-(1-ethoxycarbonylethoxy)-1,2,4-1H-triazole

Six g of 1-(4-chlorophenyl)-3-hydroxy-1,2,4-1H-triazole was added to a suspension of 1.5 g of sodium hydride in 225 ml of dimethylsulfoxide. The mixture was heated on the steam bath for 90 minutes. Then 5.5 g of ethyl 2-bromopropionate was added and the mixture was heated for 90 minutes more. It was then cooled and poured over ice-water, and the solid was collected, dried and recrystallized from toluene to obtain 1.5 g of the desired product, m.p. 62°–64°.

Theory: C, 52.80; H, 4.77; N, 14.21; Found: C, 52.89; H, 4.89; N, 14.08.

EXAMPLE 13

1-(4-chlorophenyl)-3-(1-ethoxycarbonylethoxy)-5-methyl-1,2,4-1H-triazole

The process was carried out as described in Example 4, except that the product was purified by chromatography on a silica gel column, eluting with 1–2 ethyl acetate-hexane. The materials were 0.5 g of sodium, 15 ml of methanol, 50 ml of dimethylsulfoxide, 4.9 g of 1-(4-chlorophenyl)-3-hydroxy-5-methyl-1,2,4-1H-triazole and 4.2 g of ethyl 2-bromopropionate. The yield was 4.5 g of the desired product, an oil.

Theory: C, 54.29; H, 5.21; N, 13.57; Found: C, 54.04; H, 5.39; N, 13.32.

EXAMPLE 14

3-(1-ethoxycarbonylethoxy)-1-(2,6-dimethylphenyl)-1,2,4-1H-triazole

The process was carried out as described in Example 13, except that the chromatography column was eluted with 1-1 ethyl acetate-pentane. The materials were 0.8 g of sodium, 20 ml of methanol, 50 ml of dimethylsulfoxide, 6.9 g of 3-hydroxy-1-(2,6-dimethylphenyl)-1,2,4-1H-triazole and 6.6 g of ethyl 2-bromopropionate. The yield was 6 g of the desired product, an oil.

Theory: C, 62.27; H, 6.62; N, 14.52; Found: C, 61.97; H, 6.87; N, 14.31.

EXAMPLE 15

3-(1-ethoxycarbonylethoxy)-1-(3-methylphenyl)-1,2,4-triazole

The process was carried out essentially as was that of Example 7, except that the first aqueous mixture was extracted with diethyl ether, rather than with chloroform. The materials were 1.5 g of sodium, ml of methanol, 11.4 g of 3-hydroxy-1-(3-methylphenyl)-1,2,4-1H- triazole and 11.8 g of ethyl 2-bromopropionate. The yield was 12.9 g of the desired product, an oil.

Theory: C, 61.08; H, 6.22; N, 15.26; Found: C, 60.83; H, 6.09; N, 15.08.

EXAMPLE 16

3-(1-ethoxycarbonylpropoxy)-1-phenyl-1,2,4-1H-triazole

The process was carried out essentially as was Example 7 above, except that the aqueous mixture was extracted with ethyl acetate, rather than with chloroform, and the product was not distilled. The materials were 0.7 g of sodium, 20 ml of methanol, 50 ml of dimethylsulfoxide, 5 g of 3-hydroxy-1-phenyl-1,2,4-1H-triazole and 6 g of ethyl 2-bromobutyrate.

The yield was 5.2 g of the desired product, an oil.

Theory: C, 61.08; H, 6.22; N, 15.26; Found: C, 60.82; H, 6.37; N, 14.99.

EXAMPLE 17

1-(3-chlorophenyl)-3-(1-ethoxycarbonylethoxy)-5-methyl-1,2,4-1H-triazole

The process was carried out as was Example 9 above, starting with 0.8 g of sodium, 20 ml of methanol, 75 ml of dimethylsulfoxide, 7.8 g of 1-(3-chlorophenyl)-3-hydroxy-5-methyl-1,2,4-1H-triazole and 6.7 g of ethyl 2-bromopropionate. The yield was 7.8 g of the desired product, an oil.

Theory: C, 54.29; H, 5.21; N, 13.57; Found: C, 53.97; H, 5.49; N, 13.80.

EXAMPLE 18

3-(1-ethoxycarbonylethoxy)-1-(2-methylphenyl)-1,2,4-1H-triazole

The process was carried out as was Example 4 above, except that the aqueous mixture was extracted with ethyl acetate. The process started with 0.7 g of sodium, 15 ml of methanol, 100 ml of dimethylsulfoxide, 5.4 g of 3-hydroxy-1-(2-methylphenyl)-1,2,4-1H-triazole and 5.6 g of ethyl 2-bromopropionate. The yield was 5.0 g of the desired product, an oil.

Theory: C, 61.08; H, 6.22; N, 15.26; Found: C, 61.34; H, 5.97; N, 15.03.

EXAMPLE 19

1-(4-bromophenyl)-3-(1-ethoxycarbonylethoxy)-1,2,4-1H-triazole

A 3.9 g portion of sodium was dissolved in 50 ml of ethanol and was added to a solution of 41 g of 1-(4-bromophenyl)-3-hydroxy-1,2,4-1H-triazole in 150 ml of dimethylsulfoxide. The mixture was heated at 60° for 45 minutes, and then 30.9 g of ethyl 2-bromopropionate was added. The mixture was heated for 2 hours more, and was then cooled and poured over ice-water. The solid was collected and dried, and was recrystallized from toluene. The mother liquor was concentrated under vacuum, and the residue was recrystallized from ethanol. That product was combined with the first portion of product and recrystallized from ethanol to obtain 27.9 g of the desired product, m.p. 64°-66°.

Theory: C, 45.90; H, 4.15; N, 12.35; Found: C, 45.77; H, 3.96; N, 12.39.

EXAMPLE 20

1-(3-bromophenyl)-3-(1-ethoxycarbonylethoxy)-1,2,4-1H-triazole

The process was carried out as described in Example 3, starting with 2.8 g of sodium, 50 ml of ethanol, 75 ml of dimethylsulfoxide, 29 g of 1-(3-bromophenyl)-3-hydroxy-1,2,4-1H-triazole and 21.9 g of ethyl 2-bromopropionate. The yield was 31.8 g of the desired product, m.p. 83°-85°.

Theory: C, 45.90; H, 4.15; N, 12.35; Found: C, 46.11; H, 3.91; N, 12.32.

EXAMPLE 21

1-(3,4-dichlorophenyl)-3-(1-ethoxycarbonylpropxy)-1,2,4-1H-triazole

The process was carried out as was Example 4, starting with 0.4 g of sodium, 20 ml of methanol, 75 ml of dimethylsulfoxide, 4 g of 1-(3,4-dichlorophenyl)-3-hydroxy-1,2,4-1H-triazole and 3.4 g of ethyl 2-bromobutyrate. The yield was 6 g of impure product, containing both the ethyl and methyl esters. The product was not purified but was hydrolyzed in Example 33 below.

EXAMPLE 22

3-(1-carboxyethoxy)-1-phenyl-1,2,4-1H-triazole

A 2.5 g portion of the compound of Example 1 and 2.2 g of potassium hydroxide were added to 50 ml of ethanol, and the mixture was refluxed for 3 hours. It was then poured into ice-water and the mixture was made acid with concentrated hydrochloric acid. The solid was collected and crystallized from ethanol to obtain 0.9 g of the desired product, m.p. 140°-142°.

Theory: C, 56.65; H, 4.75; N, 18.02; Found: C, 56.32; H, 4.36; N, 17.91.

EXAMPLE 23

3-(1-carboxyethoxy)-1-(2,4-dichlorophenyl)-1,2,4-1H-triazole

Seven g of the compound of Example 2 was refluxed for 3 hours with 2.4 g of potassium hydroxide in 100 ml of ethanol, and the product was collected as shown in Example 22 and recrystallized from toluene to obtain 2.3 g of the desired product, m.p. 151°-153°.

Theory: C, 43.73; H, 3.00; N, 13.91; Found: C, 43.96; H, 3.25; N, 13.69.

EXAMPLE 24

3-(1-carboxyethoxy)-1-(3-trifluoromethylphenyl)-1,2,4-1H-triazole

Fifteen g of the compound of Example 3 was refluxed for 3 hours with 5.1 g of potassium hydroxide in 150 ml of ethanol, and the product was collected as shown in Example 22 and recrystallized from ethanol to obtain 11.8 g of the desired product, m.p. 206°-208°.

Theory: C, 47.85; H, 3.35; N, 13.95; Found: C, 47.93; H, 3.52; N, 13.93.

EXAMPLE 25

3-(1-carboxyethoxy)-1-(3-chlorophenyl)-1,2,4-1H-triazole

A 6.7 g portion of the compound of Example 5 was refluxed for 3 hours with 2.5 g of potassium hydroxide in 100 ml of ethanol and the product was collected as shown in Example 22 and recrystallized from ethanol to obtain 5.2 g of the desired product, m.p. 197°–199°.

Theory: C, 49.36; H, 3.77; N, 15.70; Found: C, 49.42; H, 3.69; N, 15.60.

EXAMPLE 26

3-(1-carboxyethoxy)-1-(2-chlorophenyl)-1,2,4-1H-triazole

Ten g of the compound of Example 4 was refluxed for 4 hours with 3.8 g of potassium hydroxide in 100 ml of ethanol, and the product was collected as shown in Example 22 and recrystallized from toluene and then from ethanol to obtain 3.1 g of the desired product, m.p. 104°–106°.

Theory: C, 49.36; H, 3.77; N, 15.70; Found: C, 49.12; H, 3.79; N, 15.49.

EXAMPLE 27

3-(1-carboxyethoxy)-1-(4-chlorophenyl)-1,2,4-1H-triazole

Three g of the compound of Example 12 was refluxed for 2 hours with 1.1 g of potassium hydroxide in 100 ml of ethanol, and the product was collected as shown in Example 22 and was recrystallized from ethyl acetate to obtain 1.9 g of the desired product, m.p. 196°–198°.

Theory: C, 49.36; H, 3.77; N, 15.70; Found: C, 49.17; H, 3.97; N, 15.46.

EXAMPLE 28

3-(1-carboxyethoxy)-1-(3,4-dichlorophenyl)-1,2,4-1H-triazole

Four g of the compound of Example 6 was refluxed for 4 hours with 1.4 g of potassium hydroxide in 75 ml of ethanol, and the product was collected as shown in Example 22 and recrystallized from ethanol to obtain 3.3 g of the desired product, m.p. 222°–224°.

Theory: C, 43.73; H, 3.00; N, 13.91; Found: C, 44.01; H, 3.01; N, 13.83.

EXAMPLE 29

3-(1-carboxyethoxy)-5-methyl-1-phenyl-1,2,4-1H-triazole

Ten g of the compound of Example 7 was refluxed for 4 hours with 4.1 g of potassium hydroxide in 150 ml of ethanol and the product was collected by extraction with ethyl acetate. The extract was washed with water, dried and evaporated under vacuum, and the residue was recrystallized from toluene to obtain 2.1 g of the desired product, m.p. 157°–159°.

Theory: C, 58.29; H, 5.30; N, 16.99; Found: C, 58.13; H, 5.32; N, 16.85.

EXAMPLE 30

3-(1-carboxyethoxy)-1-(4-methoxyphenyl)-1,2,4-1H-triazole

Four g of the compound of Example 8 was refluxed for 4 hours with 1.5 g of potassium hydroxide in 50 ml of ethanol, and the product was collected as shown in Example 22 and recrystallized from ethanol to obtain 2.6 g of the desired product, m.p. 155°–157°.

Theory: C, 54.75; H, 4.98; N, 15.96; Found: C, 54.51; H, 5.15; N, 15.75.

EXAMPLE 31

3-(1-carboxyethoxy)-1-(2-methylphenyl)-1,2,4-1H-triazole

Three g of the compound of Example 18 was refluxed for 4 hours with 1.2 g of potassium hydroxide in 100 ml of ethanol, and the product was collected as shown in Example 22 and recrystallized from ethanol to obtain 2.3 g of the desired product, m.p. 151°–153°.

Theory: C, 58.29; H, 5.30; N, 16.99; Found: C, 58.42; H, 5.45; N, 16.82.

EXAMPLE 32

3-(1-carboxyethoxy)-1-(3-methylphenyl)-1,2,4-1H-triazole

Five g of the compound of Example 15 was refluxed for 4 hours with 2 g of potassium hydroxide in 50 ml of ethanol, and the product was collected as shown in Example 22 and recrystallized from toluene to obtain 4.2 g of the desired product, m.p. 155°–157°.

Theory: C, 58.29; H, 5.30; N, 16.99; Found: C, 58.50; H, 5.35; N, 16.71.

EXAMPLE 33

3-(1-carboxypropoxy)-1-(3,4-dichlorophenyl)-1,2,4-1H-triazole

Six g of the product of Example 21 was refluxed for 2 hours with 2 g of potassium hydroxide in 100 ml of ethanol, and the acidified reaction mixture was extracted with chloroform. The extract was washed with water, dried with sodium sulfate and phase separation paper, and evaporated under vacuum. The residue was recrystallized from ethanol to obtain 3.6 g of the desired product, m.p. 232°–234°.

Theory: C, 45.50; H, 3.51; N, 13.29; Found: C, 45.85; H, 3.74; N, 13.08.

EXAMPLE 34

3-(1-carboxyethoxy)-1-(2,6-dimethylphenyl)-1,2,4-1H-triazole

Three g of the compound of Example 14 was refluxed for 3 hours with 1.2 g of potassium hydroxide in 100 ml of ethanol and the product was collected as shown in Example 22 to obtain 2.2 g of the desired product, m.p. 178°–180°.

Theory: C, 59.76; H, 5.79; N, 16.08; Found: C, 59.79; H, 6.02; N, 15.82.

EXAMPLE 35

3-(1-carboxyethoxy)-1-(4-methylphenyl)-1,2,4-1H-triazole

A 2.5 g portion of the compound of Example 11 was refluxed for 4 hours with 1 g of potassium hydroxide in 50 ml of ethanol, and the product was collected as described in Example 22 to obtain 2.0 g of the desired product, m.p. 163°–165°.

Theory: C, 58.29; H, 5.30; N, 16.99; Found: C, 58.06; H, 5.03; N, 16.79.

EXAMPLE 36

3-(1-carboxyethoxy)-1-(3-chlorophenyl)-5-methyl-1,2,4-1H-triazole

A 3.8 g portion of the compound of Example 17 was refluxed for 4 hours with 1.4 g of potassium hydroxide in 100 ml of ethanol, and the product was collected as shown in Example 22 and recrystallized from ethanol to obtain 2.8 g of the desired product, m.p. 101°–103°.

Theory: C, 51.17; H, 4.29; N, 14.92; Found: C, 51.35; H, 4.49; N, 14.84.

EXAMPLE 37

1-(4-bromophenyl)-3-(1-carboxyethoxy)-1,2,4-1H-triazole

Ten g of the compound of Example 19 was refluxed for 10 minutes with 3.3 g of potassium hydroxide in 150 ml of ethanol, and the product was collected as described in Example 22 and recrystallized from ethanol to obtain 8.0 g of the desired product, m.p. 195°–197°.

Theory: C, 42.33; H, 3.23; N, 13.46; Found: C, 42.23; H, 3.35; N, 13.36.

EXAMPLE 38

1-(3-bromophenyl)-3-(1-carboxyethoxy)-1,2,4-1H-triazole

A 28.8 g portion of the compound of Example 20 was refluxed for 10 minutes with 9.5 g of potassium hydroxide in 100 ml of ethanol, and the product was collected as shown in Example 22 and recrystallized from ethanol to obtain 21.6 g of the desired product, m.p. 198°–200°.

Theory: C, 42.33; H, 3.23; N, 13.46; Found: C, 42.51; H, 3.45; N, 13.24.

EXAMPLE 39

1-(2,4-dichlorophenyl)-3-(1-methoxycarbonylethoxy)-1,2,4-1H-triazole

Three g of the compound of Example 23 was added to 75 ml of toluene and 5 ml of thionyl chloride, and the solution was heated under reflux for 2 hours. It was then cooled and evaporated under vacuum. Fifty ml of toluene was added to the residue, and that solvent was also removed under vacuum. To the residue was then added 50 ml of methanol, and the solution was heated under reflux for 2 hours, cooled and evaporated under vacuum. The residue was recrystallized from toluene to obtain 0.68 g of the desired product, m.p. 74°–75°.

Theory: C, 45.59; H, 3.51; N, 13.29; Found: C, 45.70; H, 3.34; N, 13.37.

EXAMPLE 40

1-(2,4-dichlorophenyl)-3-(1-isopropoxycarbonylethoxy)-1,2,4-1H-triazole

Three g of the compound of Example 23 was added to 50 ml of toluene, and 5 ml of thionyl chloride was then added. The mixture was heated under reflux for 2 hours, and was then cooled and evaporated under vacuum. Fifty ml of additional toluene was added and removed under vacuum, and then 50 ml of isopropanol was added to the residue. The mixture was heated under reflux for 2 hours, and was then cooled and evaporated under vacuum. The residue was recrystallized from isopropanol to obtain 2.6 g of the desired product, m.p. 55°–57°.

Theory: C, 48.85; H, 4.39; N, 12.21; Found: C, 48.60; H, 4.35; N, 12.00.

EXAMPLE 41

3-(1-benzyloxycarbonylethoxy)-1-phenyl-1,2,4-1H-triazole

A 5.5 g portion of the compound of Example 22 was added to 50 ml of methanol containing 0.54 g of sodium, and the mixture was heated briefly to reflux. It was then cooled and the solvent was removed under vacuum. To it was added 75 ml of toluene, 2.6 ml of benzyl chloride and 2.3 g of triethylamine, and the mixture was heated under reflux for 22 hours. It was then cooled, poured over ice-water, and extracted with ethyl acetate. The extract was washed with water and with saturated brine, and was dried with sodium sulfate and phase separation paper. It was then evaporated under vacuum, and the residue was recrystallized from ethanol-water to obtain 2.5 g of the desired product, m.p. 78°–80°.

Theory: C, 66.86; H, 5.30; N, 13.00; Found: C, 66.73; H, 5.02; N, 13.07.

EXAMPLE 42

3-(1-methoxycarbonylethoxy)-1-(3-trifluoromethylphenyl)-1,2,4-1H-triazole

A 2.5 g portion of the compound of Example 24 was added to 50 ml of toluene, and 3 ml of thionyl chloride was added to the mixture. It was heated under reflux for 2 hours, and was then cooled and evaporated under vacuum. Fifty ml of toluene was added to the residue and was removed under vacuum, and the residue was then taken up in methanol and heated under reflux for 3 hours. The solvent was then removed under vacuum, and the residue was recrystallized from methanol to obtain 2.0 g of the desired product, m.p. 135°–137°.

Theory: C, 49.53; H, 3.84; N, 13.33; Found: C, 49.25; H, 3.64; N, 13.36.

EXAMPLE 43

3-(1-isopropoxycarbonylethoxy)-1-(3-trifluoromethylphenyl)-1,2,4-1H-triazole

The process was carried out according to Example 42, using isopropanol instead of methanol. The product was recrystallized from toluene to obtain 0.9 g of the desired product, m.p. 97°–99°.

Theory: C, 52.48; H, 4.70; N, 12.24; Found: C, 52.27; H, 4.43; N, 12.44.

EXAMPLE 44

3-(1-methylaminocarbonylethoxy)-1-phenyl-1,2,4-1H-triazole

A 2.5 g portion of the compound of Example 1 was combined with 10 ml of 40% aqueous methylamine and 20 ml of dimethylformamide at room temperature, and the mixture was allowed to stand for 2 days. It was then poured into ice-water, and the solid was collected and air-dried to obtain 0.4 g of the desired product, m.p. 134°–135°.

Theory: C, 58.53; H, 5.73; N, 22.75; Found: C, 58.51; H, 5.82; N, 22.54.

EXAMPLE 45

3-(1-dimethylaminocarbonylethoxy)-1-(3-trifluoromethylphenyl)-1,2,4-1H-triazole

Three g of the compound of Example 24 was dissolved in 20 ml of dimethylformamide, and 3.4 g of carbonyldiimidazole was added to it. The mixture was stirred at ambient temperature for 20 minutes, and then 4 ml of 40% aqueous dimethylamine was added and the mixture was stirred at ambient temperature for 1 day. It was then poured into ice-water, and the solid was collected, dried and recrystallized from ethanol to obtain 1.5 g of the desired product, m.p. 126°–127°.

Theory: C, 51.22; H, 4.61; N, 17.07; Found: C, 50.98; H, 4.41; N, 16.99.

EXAMPLE 46

3-(1-aminocarbonylethoxy)-1-(3-trifluoromethylphenyl)-1,2,4-1H-triazole

The process was carried out as was Example 45, starting with 5 g of the compound of Example 24, 4 g of carbonyldiimidazole and 1.2 g of ammonium hydroxide. The yield was 2.8 g of the desired product, m.p. 147°–149°.

Theory: C, 48.01; H, 3.69; N, 18.66; Found: C, 47.85; H, 3.63; N, 18.60.

EXAMPLE 47

1-(3-chlorophenyl)-3-(1-dimethylaminocarbonylethoxy)-1,2,4-1H-triazole

The process was carried out as was Example 45, starting with 3 g of the compound of Example 25, 2.7 g of carbonyldiimidazole and 3.6 ml of 40% aqueous dimethylamine. The product was recrystallized from toluene to obtain 2.2 g of desired product, m.p. 136°–139°.

Theory: C, 52.98; H, 5.13; N, 19.01; Found: C, 52.93; H, 4.88; N, 18.89.

EXAMPLE 48

1-(3-chlorophenyl)-3-(1-methylaminocarbonylethoxy)-1,2,4-1H-triazole

The process was carried out as was Example 45, starting with 3 g of the compound of Example 25, 2.7 g of carbonyldiimidazole, and 3 ml of 40% aqueous methylamine. The product was recrystallized from toluene to obtain 2.3 g of the desired product, m.p. 120°–122°.

Theory: C, 51.35; H, 4.67; N, 19.96; Found: C, 51.63; H, 4.89; N, 19.83.

EXAMPLE 49

1-(3-chlorophenyl)-3-(1-aminocarbonylethoxy)-1,2,4-1H-triazole

The process was carried out as was Example 45, starting with 2.8 g of the compound of Example 25, 2.5 g of carbonyldiimidazole and 4 ml of ammonium hydroxide. The product was recrystallized from toluene and then from ethanol to obtain 1.3 g of the desired product, m.p. 143°–145°.

Theory: C, 49.54; H, 4.16; N, 21.01; Found: C, 49.72; H, 3.96; N, 21.20.

EXAMPLE 50

3-(1-methylaminocarbonylethoxy)-1-(3-trifluoromethylphenyl)-1,2,4-1H-triazole

The process was carried out as was Example 45, starting with 3 g of the compound of Example 24, 3.4 g of carbonyldiimidazole and 3 ml of 40% aqueous methylamine. The product was not recrystallized, and amounted to 2.7 g of the desired product, m.p. 137°–139°.

Theory: C, 49.96; H, 4.17; N, 17.83; Found: C, 49.84; H, 3.94; N, 17.82.

EXAMPLE 51

3-(1-ethylaminocarbonylethoxy)-1-(3-trifluoromethylphenyl)-1,2,4-1H-triazole

The process was carried out as was Example 45, starting with 3 g of the compound of Example 24, 3.4 g of carbonyldiimidazole and 2 ml of 70% aqueous ethylamine. The product was recrystallized from ethanol to obtain 1.3 g of the desired product, m.p. 135°–137°.

Theory: C, 51.22; H, 4.61; N, 17.07; Found: C, 51.46; H, 4.62; N, 16.86.

EXAMPLE 52

3-(1-aminocarbonylethoxy)-1-(4-bromophenyl)-1,2,4-triazole

The process was carried out as was Example 45, starting with 3 g of the compound of Example 37, 2.6 g of carbonyldiimidazole and 0.7 g of ammonium hydroxide. The product was recrystallized from ethanol to obtain 1.6 g of the desired product, m.p. 179°–181°.

Theory: C, 42.46; H, 3.56; N, 18.01; Found: C, 42.69; H, 3.81; N, 17.91.

EXAMPLE 53

1-(4-bromophenyl)-3-(1-methylaminocarbonylethoxy)-1,2,4-1H-triazole

The process was carried out as was Example 45, starting with 3 g of the compound of Example 37, 2.3 g of carbonyldiimidazole and 2 ml of 40% aqueous methylamine. The product was recrystallized from ethanol to obtain 2.5 g of the desired product, m.p. 176°–178°.

Theory: C, 44.33; H, 4.03; N, 17.23; Found: C, 44.54; H, 4.23; N, 17.18.

EXAMPLE 54

3-(1-aminocarbonylethoxy)-1-(3-bromophenyl)-1,2,4-1H-triazole

The process was carried out as was Example 45, starting with 3 g of the compound of Example 38, 2.3 g of carbonyldiimidazole and 0.7 g of ammonium hydroxide. A yield of 1.6 g of the desired product, in unrecrystallized form, m.p. 141°–144°, was obtained.

Theory: C, 42.46; H, 3.56; N, 18.01; Found: C, 42.70; H, 3.69; N, 17.79.

Preparation 6

3-(1-chlorocarbonylethoxy)-1-phenyl-1,2,4-1H-triazole

A 22.8 g portion of the compound of Example 22 was suspended in 150 ml of toluene, and 49 ml of thionyl chloride was added. The mixture was heated under reflux for 2 hours, and was then cooled and evaporated under vacuum. One hundred ml of additional toluene was added and was removed under vacuum, and the residue was recrystallized from toluene.

EXAMPLE 55

3-(1-methoxycarbonylethoxy)-1-phenyl-1,2,4-1H-triazole

Three g of the compound of Preparation 6 was added to 75 ml of methanol, and the solution was refluxed for an hour. It was then cooled and the solvent was removed under vacuum. The residue was taken up in 100 ml of diethyl ether, and the solution was washed with water and with saturated brine, and was dried with sodium sulfate and phase separation paper. The ether was removed under vacuum, and the residue was recrystallized from methanol to obtain 1.4 g of the desired product, m p. 88°–90°.

Theory: C, 58.29; H, 5.30; N, 16.99; Found: C, 58.16; H, 5.11; N, 16.88.

EXAMPLE 56

3-(1-isopropoxycarbonylethoxy)-1-phenyl-1,2,4-1H-triazole

Three g of the compound of Preparation 6 was added to 75 ml of isopropanol, and the solution was heated under reflux for 19 hours. It was then cooled and evaporated under vacuum, and the residue was recrystallized from toluene to obtain 1.1 g of the desired product, m.p. 104°.

Theory: C, 61.08; H, 6.22; N, 15.26; Found: C, 60.90; H, 5.98; N, 15.19.

EXAMPLE 57

3-(1-ethoxycarbonylethoxy)-1-(3-fluorophenyl)-1,2,4-1H-triazole

A 1.7 g portion of sodium was dissolved in 50 ml of absolute ethanol, and that solution was added to a solution of 13.3 g of 1-(3-fluorophenyl)-3-hydroxy-1,2,4-1H-triazole in 150 ml of dimethylsulfoxide. The solution was heated on the steam bath for 15 minutes, and then 13.5 g of ethyl 2-bromopropionate was added and the mixture was held on the steam bath for 2 hours. It was then poured over ice-water, and the aqueous mixture was extracted with diethyl ether. The organic layer was washed with water and with brine, and was then dried with sodium sulfate and phase separation paper. The solvent was removed under vacuum, and the product was recrystallized from aqueous ethanol to obtain 6.7 g of the desired product, m.p. 35°-37°.

Theory: C, 55.91; H, 5.05; N, 15.05; Found: C, 55.68; H, 5.03; N, 14.82.

EXAMPLE 58

3-(1-carboxyethoxy)-1-(3-fluorophenyl)-1,2,4-1H-triazole

Four g of the product of Example 57 was combined with 1.6 g of potassium hydroxide in 100 ml of ethanol, and the mixture was heated briefly to reflux. It was then cooled poured over ice-water, and made acid with hydrochloric acid. The product was collected by filtration and dried to obtain 3.4 g of the desired compound, m.p. 177°-179°.

Theory: C, 52.59; H, 4.01; N, 16.73; Found: C, 52.76; H, 4.25; N, 16.89.

EXAMPLE 59

3-(1-aminocarbonylethoxy)-1-(3-fluorophenyl)-1,2,4-triazole

Two g of the product of Example 58 was dissolved in 10 ml of dimethylformamide and 1.9 g of carbonyldiimidazole was added. The mixture was stirred at room temperature for 20 minutes, and 0.6 g of 35% ammonium hydroxide was added. The mixture was then stirred for 20 hours at room temperature and was poured over ice-water. The product was collected by filtration and dried to obtain 1.4 g of the desired product, m.p. 156°-158°.

Theory: C, 52.80; H, 4.43; N, 22.39; Found: C, 52.50; H, 4.22; N, 22.46.

EXAMPLE 60

1-(4-bromophenyl)-3-(1-cyclopropylaminocarbonylethoxy)-1,2,4-1H-triazole

The process was carried out according to Example 59, starting with 3 g of the compound of Example 37, 2.4 g of carbonyldiimidazole and 1.1 g of cyclopropylamine. product was recrystallized from ethanol to obtain 2.6 g of the desired product, m.p. 170°-172°.

Theory: C, 47.88; H, 4.31; N, 15.95; Found: C, 47.69; H, 4.05; N, 16.19.

EXAMPLE 61

1-(4-bromophenyl)-3-(1-pyrrolidinocarbonylethoxy)-1,2,4-1H-triazole

A 2.4 g portion of carbonyldiimidazole was added to 3 g of the product of Example 37 dissolved in 20 ml of dimethylformamide and the mixture was stirred at room temperature for 20 minutes. To it was then added 1.2 g of propylamine and the mixture was stirred at room temperature for 3 days. It was then poured over ice-water, and the product was collected by filtration and dried. It was recrystallized from ethanol to obtain 2.3 g of the desired product, m.p. 144°-145°.

Theory: C, 47.61; H, 4.85; N, 15.86; Found: C, 47.85; H, 5.03; N, 15.86.

EXAMPLE 62

1-(3-bromophenyl)-3-(1-cyclopropylaminocarbonylethoxy)-1,2,4-1H-triazole

Three g of the compound of Example 38 was dissolved in 20 ml of dimethylformamide, 2.4 g of carbonyldiimidazole was added, and the solution was stirred at room temperature for 20 minutes. To it was added 1.1 g of cyclopropylamine, and the mixture was stirred for 16 hours more. It was then poured over ice-water, and the product was collected, dried and recrystallized from ethanol to obtain 2.1 g of the desired product, m.p. 134°-135°.

Theory: C, 47.88; H, 4.31; N, 15.95; Found: C, 48.01; H, 4.25; N, 15.98.

EXAMPLE 63

1-(3-bromophenyl)-3-(1-pyrrolidinocarbonylethoxy)-1,2,4-1H-triazole

Three g of the compound of Example 38 was reacted with 1.2 g of propylamine, substantially as shown in Example 62, to obtain 2.4 g of the desired product, m.p. 111°-113°.

Theory: C, 47.61; H, 4.85; N, 15.86; Found: C, 47.42; H, 4.58; N, 15.67.

EXAMPLE 64

3-(1-ethoxycarbonylethoxy)-1-(4-trifluoromethylphenyl)-1,2,4-1H-triazole

A 0.54 g portion of sodium was dissolved in 15 ml of absolute ethanol, and was added to 50 ml of dimethylsulfoxide containing 5.4 g of 3-hydroxy-1-(4-trifluoromethylphenyl)-1,2,4-1H-triazole. An additional 25 ml of dimethylsulfoxide was added, and the mixture was heated on the steam bath for 15 minutes. Then 4.3 g of ethyl 2-bromopropionate was added and heating was continued for 1 hour. The mixture was then cooled and poured over ice-water, and the product was collected, dried, and purified by high-performance liquid chromatography, eluting with 1:1 hexane:ethyl acetate. The product-containing fractions were combined and evaporated under vacuum to obtain 3.5 g of the desired product.

Theory: C, 51.07; H, 4.29; N, 12.76; Found: C, 51.27; H, 4.42; N, 12.85.

EXAMPLE 65

3-(1-carboxyethoxy)-1-(4-trifluoromethylphenyl)-1,2,4-1H-triazole

A 17.1 g portion of the compound of Example 64, prepared in successive reactions, was hydrolyzed with 5.8 g of potassium hydroxide, substantially as shown in Example 58, to obtain 15.5 g of the desired product, m.p. 215°–218°.

Theory: C, 47.85; H, 3.35; N, 13.95; Found: C, 48.04; H, 3.27; N, 13.95.

EXAMPLE 66

3-(1-aminocarbonylethoxy)-1-(4-trifluoromethylphenyl)-1,2,4-1H-triazole

Three g of the product of Example 65 was reacted with 0.7 g of 35% ammonium hydroxide, substantially as shown in Example 60, to obtain 2 g of the desired product, m.p. 178°–180°.

Theory: C, 48.01; H, 3.69; N, 18.66; Found: C, 47.80; H, 3.52; N, 18.54.

EXAMPLE 67

3-(1-dimethylaminocarbonylethoxy)-1-(4-trifluoromethylphenyl)-1,2,4-1H-triazole

Three g of the product of Example 65 was reacted with 4 ml of 45% aqueous dimethylamine, substantially as shown in Example 60, to obtain 1.2 g of the desired product, m.p. 102°–104°.

Theory: C, 51.22; H, 4.61; N, 17.07; Found: C, 51.04; H, 4.67; N, 17.10.

EXAMPLE 68

3-(1-cyclopropylaminocarbonylethoxy)-1-(4-trifluoromethylphenyl)-1,2,4-1H-triazole Three g of the product of Example 65 was reacted with 1.1 g of cyclopropylamine, substantially as shown in Example 60, to obtain 2.6 g of the desired product, m.p. 175°–177°.

Theory: C, 52.94; H, 4.44; N, 16.46; Found: C, 52.73; H, 4.26; N, 16.60.

EXAMPLE 69

3-(1-methylaminocarbonylethoxy)-1-(4-trifluoromethylphenyl)-1,2,4-1H-triazole

Three g of the product of Example 65 was reacted with 2 ml of aqueous methylamine, substantially as shown in Example 60, to obtain 2.3 g of the desired product, m.p. 157°–158°.

Theory: C, 49.69; H, 4.17; N, 17.83; Found: C, 49.64; H, 4.23; N, 18.04.

EXAMPLE 70

3-(1-ethoxycarbonylethylthio)-1-phenyl-1,2,4-1H-triazole

Three g of 1-phenyl-3-thiono-1,2,4-1H-triazole was suspended in 50 ml of ethanol, and to it was added 0.8 g of sodium hydroxide in 30 ml of ethanol. The mixture was heated to reflux for 15 minutes, and then 3 g of ethyl 2-bromopropionate was added and the mixture was held at reflux for 2 hours. It was then cooled, poured over ice-water, and extracted with ethyl acetate. The organic layer was washed with water, with 2N aqueous sodium hydroxide and with brine, and was dried with sodium sulfate and phase separation paper. The solvent was removed under vacuum, and the residue was purified by high-performance liquid chromatography, with 4:1 hexane:ethyl acetate as the solvent. The product-containing fractions were combined and evaporated under vacuum to obtain 1.8 g of the desired product.

Theory: C, 56.30; H, 5.45; N, 15.15; Found: C, 56.60; H, 5.23; N, 15.34.

EXAMPLE 71

1-(3,4-dichlorophenyl)-3-(1-ethoxycarbonylethylthio)-1,2,4-1H-triazole

An 11.5 g portion of 1-(3,4-dichlorophenyl)3-thiono-1,2,4-1H-triazole was dissolved in 100 ml of dry dimethylsulfoxide, and was added to 1.1 g of sodium dissolved in 50 ml of absolute ethanol. The mixture was warmed at 60°–80° for 1 hour, and then 8.5 g of ethyl 2-bromopropionate was added and the mixture was held at 100°–110° for 2 hours. It was then cooled and poured over ice-water, and the aqueous mixture was extracted with dichloromethane. The organic layer was washed with brine, and was dried over magnesium sulfate. The solvent was removed under vacuum, and the residue was purified by chromatography, eluting with 2:1 hexane:ethyl acetate. The product-containing fractions were combined and evaporated under vacuum to obtain 11 g of the desired product.

Theory: C, 45.10; H, 3.78; N, 12.14; Found: C, 44.91; H, 3.72; N, 11.87.

EXAMPLE 72

3-(1-ethoxycarbonylethoxy)-1-(4-trifluoromethoxyphenyl)-1,2,4-1H-triazole

Eleven g of 3-hydroxy-1-(4-trifluoromethoxyphenyl)-1,2,4-1H-triazole was dissolved in 100 ml of dimethylsulfoxide, and to it was added a solution of sodium ethoxide prepared from 1.2 g of sodium and 20 ml of absolute ethanol. An additional 100 ml of dimethylsulfoxide was added, and the solution was heated on the steam bath for 90 minutes. Then 8.3 g of ethyl 2-bromopropionate was added, and heating was continued for 90 minutes more. The solution was cooled and poured over ice water, and the solid was collected and dried to obtain 15 g of the desired product, m.p. 52°–53°.

Theory: C, 48.70; H, 4.09; N, 12.17; Found: C, 48.93; H, 4.21; N, 12.34.

EXAMPLE 73

3-(1-carboxyethoxy)-1-(4-trifluoromethoxyphenyl)-1,2,4-1H-triazole

Thirteen g of the compound of Example 72 was deesterified according to the process of Example 22, and the product was isolated and purified, following the same Example, to obtain 6.8 g of the desired product, m.p. 200°–203°.

Theory: C, 45.44; H, 3.18; N, 13.25; Found: C, 45.20; H, 3.16; N, 13.08.

EXAMPLE 74

1-(3,5-dichlorophenyl)-3-(1-ethoxycarbonylethoxy)-1,2,4-1H-triazole

A 1.8 g portion of sodium was dissolved in 75 ml of absolute ethanol, and the solution was added slowly with stirring to a solution of 18.5 g of 1-(3,5-dichlorophenyl)-3-hydroxy-1,2,4-1H-triazole in 200 ml of dimethylsulfoxide. The solution was stirred at 60° for 1 hour, 14.5 g of ethyl 2-bromopropionate was added, and the mixture was heated for 2 hours at 100°–110°. It was then poured over ice water, and the solid was collected, dried and recrystallized from ether to obtain 10 g of the desired product. The mother liquor was chromatographed to obtain 1.3 g of additional product.

Theory: C, 47.29; H, 3.97; N, 12.73; Found: C, 47.07; H, 4.03; N, 12.57.

EXAMPLE 75

3-(1-carboxyethoxy)-1-(3,5-dichlorophenyl)-1,2,4-1H-triazole

An 11.3 g portion of the product of Example 74 was deesterified according to the process of Example 22, and was recrystallized from ethanol/dichloromethane to obtain 10.5 g of the desired product, m.p. 230°–231°.

Theory: C, 43.73; H, 3.00; N, 13.91; Found: C, 44.08; H, 3.24; N, 13.63.

Testing

Representative compounds of the invention have been tested in standardized test methods designed to evaluate their ability to regulate the growth of plants, particularly of soybeans. The following reports of such tests illustrate the activity of the compounds.

Test I

Plant Physiology Screen

A. 15.0 lb/A Test

The compounds submitted to this test were applied both pre- and post-emergence on tomato (*Lycopersicon esculentum*), large crabgrass (*Digitaria sanguinalis*), and redroot pigweed (*Amaranthus retroflexus*) to determine the ability of the compounds to affect growth of these plants in various ways. The compounds were formulated for testing by dissolving a 15 mg sample of the compound in 0.6 ml of 1:1 acetone-ethanol containing a small amount of a blended anionic-nonionic surfactant, and the solution was diluted with deionized water to a final volume of 6.0 ml. Each formulated compound was applied uniformly over one 66-mm square pot soon after the seeds were planted (pre-emergence) and to the foliage of the established plants (post-emergence) 12 days after the seeds were planted, each pot receiving 3.0 ml of the formulation.

The treated plants were allowed to grow out in the greenhouse with normal watering and exposure to light, and they were observed 13 days after treatment, using the following rating scale for plant effect and indications of symptoms.

A. Rating Scale For Plant Effect
 1=no effect
 2=slight effect
 3=moderate effect
 4=severe effect
 5=no emergence or death of plant
B. Symptoms
 A=Abscission of leaves
 B=Burned
 C=Chlorosis
 D=Death
 E=Epinasty
 F=Formative effects other than epinasty
 G=Dark green
 I=Increased growth
 L=Local necrosis N=No germination
 P=Purple pigmentation
 R=Reduced germination
 S=Stunting
 Y=Delayed senescence
 Z=Increased branching

B. 8.0 lb/A Test

The compounds submitted to this test were applied either pre-emergence only, post-emergence only, or both pre- and post-emergence on species of the following group to determine the ability of the compounds to affect growth of those plants in various ways.
 Soybean (*Glycine max*)
 Barley (*Hordeum vulgare*)
 Mustard (*Brassica* sp.)
 Large Crabgrass (*Digitaria sanguinalis*)
 Morningglory (*Ipomoea* sp.)
 Foxtail Millet (*Setaria italica*)
 Velvetleaf (*Abutilon theophrasti*)
 Wildoat (*Avena fatua*)
 Tomato (*Lycopersicon esculentum*)
 Redroot Pigweed (*Amaranthus retroflexus*)
 Barnyardgrass (*Echinochloa crus-galli*)
 Zinnia (*Zinnia elegans*)

Seeds of the species to be tested were planted in a flat pan in a sterile greenhouse soil mixture. Post-emergence applications were sprayed over the established plants 9 days after the seeds were planted and pre-emergence applications were applied to the soil soon after the seeds were planted.

The compounds were formulated for testing by dissolving a 60 mg sample for either a pre- or post-emergence application or a 120 mg sample for both a pre- and a post-emergence application in either 1.25 ml or 2.5 ml of 1:1 acetone-ethanol containing a small amount of a blended anionic-nonionic surfactant. The solution was diluted with deionized water to 12.5 ml for pre-emergence only or post-emergence only or to 25.0 ml for both pre- and post-emergence applications.

The treated plants were allowed to grow out in the greenhouse with normal watering and exposure to light, and the post-emergence applications were observed 12 to 14 days after treatment while the pre-emergence applications were observed 18 to 21 days after treatment using the rating scale for plant effect and symptoms as described earlier.

C. 4.0 lb/A and Lower Rates Test

The compounds submitted to this test were applied either pre-emergence only, post-emergence only, or both pre- and post-emergence on species of the following group to determine the ability of the compounds to effect growth of the plants.
 Corn (*Zea mays*)
 Soybean (*Glycine max*)
 Wheat (*Triticum aestivum*)
 Barley (*Hordeum vulgare*)
 Rice (*Oryza sativa*)
 Cotton (*Gossypium hirsutum*)
 Sugarbeet (*Beta vulgaris*)

Seeds were planted in flat pans in a sterile greenhouse soil mixture. Post-emergence applications were sprayed over the established plants 9 days after the seeds were planted and the pre-emergence applications were applied to the soil soon after the seeds were planted.

The compounds were formulated for testing by dissolving a 120 mg sample for either a pre-emergence or a post-emergence application or a 240 mg sample for both a pre- and a post-emergence application in either 5 ml or 10 ml of 1:1 acetone-ethanol containing a small amount of a blended anionic-nonionic surfactant, and the solution was diluted with deionized water to 50 ml for pre-emergence or post-emergence only or to 100 ml for both pre- and post-emergence applications. Each pan of seeds or plants was sprayed with 12.5 ml of the formulated compound, and the remaining one-half of the formulation was then serially diluted to acquire the other lower concentrations.

The treated plants were allowed to grow out in the greenhouse with normal watering and exposure to light, and the post-emergence applications were observed 12 to 14 days after treatment while the pre-emergence applications were observed 18 to 21 days after treatment.

In some tests the effects of the plants were rated on a 0–9 scale, which is an expanded version of the 1–5 scale explained above.

The following tables present the results of testing various compounds. In each table, the application rates are shown, in pounds per acre, below the compounds' example numbers.

TABLE I

POSTEMERGENCE
0-9 SCALE

| | Example 1 | | | Example 2 | | | Example 23 | | Example 3 | | | Example 55 | | | Example 40 | | | Example 24 | |
|---|---|---|---|---|---|---|---|---|---|---|---|---|---|---|---|---|---|---|---|
| | 1 | 0.12 | 4 | 0.12 | 0.5 | 1 | 0.12 | 1 | 0.12 | 1 | 2 | 1 | 0.12 | 0.5 | 1 | 0.12 | 0.5 | 1 | 0.12 |
| Corn | 9SGF* | 0 | 2F | 0 | 0 | 0 | 0 | 0 | 0 | 0 | 0 | 0 | 0 | 0 | 0 | 0 | 0 | 0 | 0 |
| Soybean | 4SGF | 4SGF | 9SFGB | 7SGF | 8SGF | 9SFG | 7SGF | 9SFG | 6SGF | 8SFG | 8SFG | 8SFG | 3SG | 7SGF | 6FSG | 8SFG | 7SGF | 8SFG | 8SGF |
| Wheat | 0 | 0 | 7SF | 0 | 2S | 6SF | 0 | 7SF | 0 | 0 | 0 | 0 | 0 | 0 | 0 | 6SF | 0 | 0 | 0 |
| Barley | 0 | 0 | 7SFB | 0 | 2S | 6SF | 0 | 5SB | 0 | 0 | 0 | 0 | 0 | 0 | 0 | 4SF | 0 | 0 | 0 |
| Rice | 4SB | 0 | 7SBF | 0 | 2S | 5SBF | 0 | 7SF | 0 | 4SFB | 3SB | 0 | 0 | 0 | 6SFG | 6SFG | 0 | 0 | 0 |
| Cotton | 7SF | 5SG | 9SBF | 4FS | 5SF | 7SF | 4SF | 4SF | 4SF | 9SF | 7SF | 7SF | 4SGF | 5SF | 6SF | 8SF | 5SF | 6FS | 6FS |
| Sugar beet | 8SF | 7S | 9SF | 6SF | 8SG | 8SF | 7SF | 7SF | 6SF | 8SF | 8SF | 8SF | 2FS | 8SF | 8SF | 8SF | 5SF | 7FS | 7FS |

| | Example 56 | | Example 4 | | | Example 26 | | Example 5 | | Example 6 | | | Example 39 | | | Example 28 | |
|---|---|---|---|---|---|---|---|---|---|---|---|---|---|---|---|---|---|
| | 2 | 0.12 | 4 | 0.12 | 0.5 | 1 | 0.12 | 2 | 1 | 2 | 1 | 0.25 | 2 | 1 | 0.12 | 1 | 0.25 |
| Corn | 7SFGZ | 7SFGZ | 0 | 0 | 0 | 0 | 3SF | 5SF | 0 | 8SFGZ | 0 | 8SFGZ | 7SFG | 8SFG | 0 | 6FSG | 0 |
| Soybean | 4SF | 0 | 9SFB | 4SG | 9SFG | 3SF | 0 | 9SFG | 5SF | 5SF | 5SF | 5SF | 2S | 3S | 0 | 0 | 0 |
| Wheat | 0 | 0 | 0 | 0 | 7SF | 0 | 0 | 7SF | 0 | 5SB | 5SB | 5SF | 0 | 2S | 0 | 0 | 0 |
| Barley | 0 | 0 | 0 | 0 | 7SF | 0 | 0 | 7SF | 0 | 3S | 5SB | — | 0 | 0 | 0 | 0 | 0 |
| Rice | 0 | 0 | 7SFB | 0 | 7SFB | 0 | 0 | 7SFB | 4SFB | 9BS | 9BS | 9BS | 5SF | 7FS | 6FS | 6FS | 7FS |
| Cotton | 5FS | 2SF | 9SFB | 5SFG | 9SFB | 4SF | 4SF | 9SB | 5SF | 9BSF | 8FBS | 7FS | 5SF | 5SF | 8SF | 8SF | 5SF |
| Sugar beet | 3F | 4FS | 9SF | 7SF | 8SF | 5SF | 3FS | 8SF | 8SF | 8FBS | 8FS | — | 7FS | 7FS | 6SF | 3FS | 5FS |

| | Example 25 | | Example 41 | | | Example 43 | | | Example 7 | | | Example 27 | | | Example 22 | |
|---|---|---|---|---|---|---|---|---|---|---|---|---|---|---|---|---|---|
| | 2 | 0.12 | 4 | 1 | 0.12 | 4 | 1 | 0.12 | 2 | 1 | 0.12 | 4 | 1 | 0.12 | 1 | 0.5 |
| Corn | 9SFG | 8SGF | 0 | 0 | 0 | 0 | 0 | 0 | 0 | 0 | 0 | 0 | 0 | 0 | 0 | 2S |
| Soybean | 4SF | 0 | 7SFG | 6SFG | 0 | 8SFG | 7SFG | 8SFG | 0 | 0 | 0 | 9SGFB | 4SFG | 4SFG | 8SFGZ | 8SGF |
| Wheat | 4SF | 0 | 0 | 0 | 0 | 0 | 0 | 0 | 0 | 0 | 0 | 7SGF* | 3SF | 0 | 3S | 3S |
| Barley | 8SBF | 0 | 0 | 0 | 0 | 3S | 0 | 0 | 0 | 0 | 0 | 7SGF | 4SF | 0 | 2S | 4S |
| Rice | 9SBF | 8FS | 7SFB | 4SFB | 0 | 0 | 7FS | 8FS | 0 | 0 | 0 | 8SF | 4SB | 0 | — | — |
| Cotton | 8SF | 8FS | 7SF | 5SF | 4SF | 7FS | 7FS | 8FS | 3SF | 4SF | 4SF | 9SF | 6SF | 4SF | 8SBF | 8SBF |
| Sugar beet | 9SF | — | — | — | — | 8SF | 8FS | 8FS | 5FS | 5FS | 0 | 9SF | 8SF | 5FS | 5FS | 5FS |

| | Example 8 | | | Example 42 | | | Example 9 | | | Example 30 | | | Example 10 | | | Example 12 | | | Example 16 | | Example 29 |
|---|---|---|---|---|---|---|---|---|---|---|---|---|---|---|---|---|---|---|---|---|---|---|
| | 0.12 | 0.25 | 0.5 | 4 | 1 | 0.12 | 4 | 1 | 0.25 | 4 | 1 | 0.25 | 1 | 0.25 | 0.12 | 1 | 0.25 | 0.12 | 0.5 | 0.12 | 0.5 | 0.5 |
| Corn | 9SFG* | 9SFG* | 0 | 0 | 0 | 0 | 0 | 0 | 0 | 0 | 0 | 0 | 0 | 0 | 0 | 6SG | 0 | 0 | 0 | 0 | 0 | 0 |
| Soybean | 6SG | 5SG | 6SFG | 9SFG* | 8SGF | 6SFG | 0 | 0 | 0 | 0 | 2S | 5SF | 0 | 0 | 0 | 9SGF* | 6SFG | 6SFG | 5SGF | 2F | 4SF | 2SFG |
| Wheat | 6SGB | 4SG | 0 | 6SG | 5SG | 0 | 0 | 0 | 0 | 2S | 0 | 0 | 0 | 0 | 0 | 6SG | 2S | 0 | 0 | 0 | 0 | 0 |
| Barley | 7SB | 5SB | 0 | 6SGB | 4SG | 0 | 0 | 0 | 0 | 0 | 0 | 0 | 0 | 0 | 0 | 7SB | 0 | 0 | 0 | 0 | 0 | 0 |
| Rice | 8SF | 8SF | 7FSG | 7SB | 5SB | 3SF | 0 | 0 | 0 | 5SGF | 6SGF | 5SF | 0 | 5SF | 7SF | 7SF | 4FS | 5SF | 6SGF | 4FS | 6FS | 0 |
| Cotton | 9SF | 9SF | 7FS | 9SFB | 8SF | 5FS | 0 | 0 | 0 | 6FS | 5FS | 3FS | 8SF | 3FS | 2FS | 8SF | 8FS | 8FS | 8SF | 0 | 3FS | 5FS |

*branching at the cotyledon nodes

TABLE II

POSTEMERGENCE
1-5 SCALE

| | Example 29 | | | | Example 7 | | | | | Example 8 | | | Example 9 |
|---|---|---|---|---|---|---|---|---|---|---|---|---|---|
| | 8 | 4 | 1 | .5 | 8 | 4 | 2 | 1 | .5 | 8 | 1 | .5 | 8 |
| Corn | 1 | 1 | 1 | | 1 | 1 | 1 | 1 | | | 1 | 1 | |
| Soybean | 2SF | 2F | 2F | 1 | 3SFZ | 3SZB | 3SZ | 2SZ | 1 | 3SFG | 3SF | 3SF | 3SFB |
| Wheat | 1 | 1 | 1 | | | 2B | 1 | 1 | 1 | | 1 | 1 | |
| Cotton | 2SF | 1 | 1 | | | 2FB | 2FB | 2S | 1 | | 3FS | 3FS | |
| Barley | 1 | 1 | 1 | 1 | 1 | 1 | 1 | 1 | 1 | 2B | 2B | 1 | 1 |
| Sugar beet | 2SF | 2SF | 1 | | | 3S | 4BS | 2BS | 1 | | 3FS | 3FS | |
| Rice | 1 | 1 | 1 | | | 2BS | 2B | 1 | 1 | | 2B | 1 | |

| | Example 30 | | | | Example 10 | Example 11 | | | | Example 31 | | | | Example 34 |
|---|---|---|---|---|---|---|---|---|---|---|---|---|---|---|
| | 8 | 4 | 1 | .5 | 8 | 8 | 4 | 2 | 1 | 8 | 4 | 1 | 1 | 8 |
| Corn | | 1 | 1 | 1 | | | 1 | 1 | 1 | | 1 | 1 | 1 | |
| Soybean | 3SFG | 4SFG | 2SG | 1 | | 2S | 2S | 1 | 1 | 3SGF | 4SFG | 2SF | 1 | 1 |
| Wheat | | 1 | 1 | 1 | 3SB | 3SFG | 1 | 1 | 1 | | 1 | 1 | 1 | |
| Cotton | | 4FS | 3FS | 3FS | | 3BS | 3S | 1 | | | 3FS | 2FS | 1 | |
| Barley | 1 | 1 | 1 | 1 | 1 | 2G | 1 | 1 | 1 | 1 | 1 | 1 | 1 | 1 |
| Sugar beet | | 4FS | 3FS | 3FS | | 3FS | 3FS | 3FS | | | 4FS | 4FS | 3FS | |
| Rice | | 1 | 1 | 1 | | 3S | 1 | 1 | | | 1 | 1 | 1 | |

| Example 44 | |
|---|---|
| | 8 |
| Tomato | 2 |
| Barnyard Grass | 2S |
| Mustard | 2FS |
| Crabgrass | 2SB |
| Pigweed | 2S |
| Velvetleaf | 2FS |
| Foxtail | 1 |
| Morningglory | 1 |
| Wildoat | 1 |
| Zinnia | 2B |

| | Example 13 | | | Example 14 | | | Example 15 | | | | Example 32 | | |
|---|---|---|---|---|---|---|---|---|---|---|---|---|---|
| | 8 | 2 | .5 | 8 | 4 | 1 | 8 | 4 | 2 | 1 | 8 | 1 | .5 |
| Corn | | 1 | 1 | | 1 | 1 | 2S | 1 | 1 | | | 1 | 1 |
| Soybean | 4SFB | 3SFZ | 2SF | 3SFB | 2S | 1 | 3SFB | 3SFZ | 2FZ | 1 | 3SF | 2Z | 1 |
| Wheat | | 2SFB | 2SF | | 2B | 1 | | 1 | 1 | 1 | | 1 | 1 |
| Cotton | | 3FS | 2F | | 2S | 1 | | 3FS | 2FS | 1 | | 2F | 1 |
| Barley | 2SB | 2SBF | 2S | 1 | 1 | 1 | 2SB | 1 | 1 | 1 | 1 | 1 | 1 |
| Sugar beet | | 3FS | 2F | 3SF | 3SF | | | 3FS | 3SF | 3SF | | 3SF | 3SF |
| Rice | | 3BS | 3BS | | 1 | 1 | | 2SB | 1 | 1 | | 1 | 1 |

| | Example 33 | | | Example 16 | | | Example 35 | | | Example 17 | | |
|---|---|---|---|---|---|---|---|---|---|---|---|---|
| | 8 | 2 | .5 | 8 | 4 | .5 | 8 | 4 | 2 | 8 | 4 | 1 |
| Corn | | 1 | 1 | | 1 | 1 | | 1 | 1 | | 2F | 1 |
| Soybean | 2S | 1 | 1 | 4SFG | 4SFG | 2F | 3SF | 3SFG | 1 | 4SGF | 4SFG | 3SFG |
| Wheat | | 1 | 1 | | 1 | 1 | | 1 | 1 | | 3SF | 2SF |
| Cotton | | 4FS | 3FS | | 3FS | 2F | | 3SFB | 1 | | 4SBF | 3SFB |
| Barley | 1 | 1 | 1 | 2S | 1 | 1 | 1 | 1 | 1 | | 2SG | 3SFB | 2SF |
| Sugar beet | | 4FS | 2FS | | 3FS | 3FS | | 3FS | 1 | | 4FS | 3FS |
| Rice | | 1 | 1 | | 2B | 1 | | 1 | 1 | | 3SFB | 2S |

| | Example 36 | | | | Example 18 | | | | Example 45 | | Example 46 | |
|---|---|---|---|---|---|---|---|---|---|---|---|---|
| | 8 | 4 | 1 | .5 | 8 | 4 | 2 | 1 | .5 | 8 | .5 | 8 | .5 |
| Corn | | 2F | 1 | 1 | 1 | 1 | 1 | 1 | 1 | | 2F | | 1 |
| Soybean | 4SGF | 3SFG | 3SFG | 3SFG | 4FSG | 3SFG | 2SFG | 2F | 1 | 3SGB | 3SGZ | 3SG | 2SBZ |
| Wheat | | 2SF | 2S | 2S | | 2B | 1 | 1 | 1 | | 2SF | | 1 |
| Cotton | | 4FS | 4FS | 4FS | | 3FS | 2FS | 2F | 2S | | 3FS | | 1 |
| Barley | 2G | 2FS | 2S | 1 | 1 | 2S | 1 | 1 | 1 | 2SB | 2SF | 2SG | 1 |
| Sugar beet | | 4FS | 5D | 4SF | | 4FS | 3FS | 1 | 2SF | | 3FS | | 2SBF |
| Rice | | 2S | 3SB | 3S | | 1 | 1 | 1 | 1 | | 1 | | 1 |

| | Example 47 | | | Example 48 | | Example 49 | | | Example 50 | | | Example 51 | |
|---|---|---|---|---|---|---|---|---|---|---|---|---|---|
| | 8 | 4 | .5 | 8 | .5 | 8 | 2 | .5 | 8 | 1 | .5 | 8 | .5 |
| Corn | | 1 | 1 | | 1 | | 1 | 1 | | 1 | 1 | | 1 |
| Soybean | 3SFB | 2SZB | 2SBZ | 3SFZ | 3SFZ | 4SFZ | 3SZF | 3SZG | 3FSZ | 3SZF | 3SZF | 1 | 3SZG |
| Wheat | | 1 | 1 | | 1 | | 2BS | 2B | | 1 | 1 | | 1 |
| Cotton | | 1 | 1 | 2FS | | | 3FS | 3FS | | 2SF | 2FS | | 2F |
| Barley | 1 | 1 | 1 | 1 | 1 | 3SFG | 3SFB | 3SB | 2S | 1 | 1 | 1 | 1 |
| Sugar beet | | 3SF | 1 | 2FS | | | 3FS | 3FS | | 2FS | 1 | | 2FS |
| Rice | | 1 | 1 | 1 | | | 2B | 1 | | 1 | 1 | | 1 |

| 15 lb/a | | | | | | | | |
|---|---|---|---|---|---|---|---|---|
| Example 22 | Example 2 | Example 4 | Example 28 | Example 8 | Example 10 | Example 12 | Example 31 | Example 14 |

TABLE II-continued

POSTEMERGENCE
1-5 SCALE

| | | | | | | | | | |
|---|---|---|---|---|---|---|---|---|---|
| Tomato | 3FS | 4FS | 4FS | 4FS | 4FS | 1 | 4FS | 3F | 1 |
| Crabgrass | 1 | 4BS | 3BS | 4FS | 2S | 4BS | 3FBS | 1 | 1 |
| Pigweed | 2FS | 5D | 5D | 5D | 5D | 4BS | 5D | 4SFB | 1 |
| | Example 33 | Example 16 | Example 15 | Example 18 | Example 45 | Example 46 | Example 48 | Example 50 | Example 51 |
| Tomato | 3FS | 4F | 4SF | 4FS | 4FS | 4FS | 3FS | 3FG | 4FS |
| Crabgrass | 1 | 4BS | 3SBF | 3BS | 1 | 4FSB | 2B | 1 | 1 |
| Pigweed | 3FBS | 4BSF | 4BFS | 4BS | 4FSB | 4FSB | 3FS | 4SFG | 4FS |
| | Example 29 | Example 34 | Example 57 | Example 19 | Example 37 | Example 20 | Example 38 | Example 62 | |
| Tomato | 3FGS | 1 | 4FS | 4FS | 4FS | 4FS | 4FS | 4FS | |
| Crabgrass | 1 | 1 | 2FS | 3SF | 3SF | 3FS | 3FS | 1 | |
| Pigweed | 1 | 1 | 4FS | 4FS | 4FS | 4FS | 4FS | 4FS | |

8 lb/a.

| | Example 58 | Example 59 | Example 60 | Example 61 | Example 63 | Example 64 | Example 65 | Example 66 | Example 68 | Example 69 |
|---|---|---|---|---|---|---|---|---|---|---|
| Tomato | 4F | 4FS | 1 | 2S | 4FS | 4FS | 3F | 2F | 1 | 1 |
| Crabgrass | 1 | 1 | 1 | 1 | 1 | 3FS | 3FS | 1 | 1 | 1 |
| Pigweed | 4FS | 4SF | 1 | 2S | 3FS | 4BS | 4FS | 2FS | 1 | 1 |

TABLE III

PREEMERGENCE
1-5 SCALE
15 lb/a

| | Example 1 | Example 22 | |
|---|---|---|---|
| Tomato | 5N | 1 | |
| Crabgrass | 4RS | 2S | |
| Pigweed | 5N | 2RS | |
| | Example 2 | Example 23 | Example 3 |
| Tomato | 2S | 1 | 2S |
| Crabgrass | 4RS | 4RS | 4RS |
| Pigweed | 4RS | 4RS | 4RS |
| | Example 55 | Example 24 | Example 6 |
| Tomato | 1 | 3F | 4RS |
| Crabgrass | 4RS | 4RS | 4RS |
| Pigweed | 4RS | 4RS | 4RS |
| | Example 4 | Example 5 | Example 40 |
| Tomato | 1 | 3F | 2F |
| Crabgrass | 4RS | 4RS | 4RS |
| Pigweed | 4RS | 4SF | 4SF |
| | Example 25 | Example 26 | Example 41 |
| Tomato | 3FS | 1 | 2RS |
| Crabgrass | 4RS | 4S | 2RS |
| Pigweed | 4SF | 4SF | 3RS |
| | Example 6 | Example 27 | |
| Tomato | 3F | 1 | |
| Crabgrass | 4RS | 4RS | |
| Pigweed | 4FS | 4RS | |
| | Example 28 | Example 42 | Example 43 |
| Tomato | 3F | 3F | 3F |
| Crabgrass | 4RS | 5N | 4RS |
| Pigweed | 4FS | 4FS | 5N |
| | Example 7 | Example 8 | Example 30 |
| Tomato | 1 | 3FS | 1 |
| Crabgrass | 1 | 2F | 4RS |
| Pigweed | 1 | 4FS | 5D |
| | Example 10 | Example 11 | Example 12 |
| Tomato | 1 | 1 | 5D |
| Crabgrass | 1 | 2S | 4BS |
| Pigweed | 1 | 2S | 5N |
| | Example 31 | Example 13 | |
| Tomato | 1 | 2SF | |
| Crabgrass | 1 | 4RS | |
| Pigweed | 1 | 5N | |
| | Example 14 | Example 32 | Example 33 |
| Tomato | 1 | 1 | 2 |
| Crabgrass | 1 | 4RS | 5D |
| Pigweed | 1 | 2S | 5D |
| | Example 16 | Example 35 | Example 15 |
| Tomato | 1 | 3RS | 2SF |
| Crabgrass | 2S | 4RS | 3RS |
| Pigweed | 3RS | 3RS | 3RS |
| | Example 17 | Example 36 | Example 18 |
| Tomato | 2F | 1 | 1 |
| Crabgrass | 4RS | 4RS | 3RS |
| Pigweed | 4SF | 2S | 1 |
| | Example 45 | Example 46 | Example 47 |
| Tomato | 2B | 4FS | 1 |
| Crabgrass | 4BS | 4RS | 3RS |
| Pigweed | 4BS | 4FS | 4BS |
| | Example 48 | Example 49 | Example 50 |
| Tomato | 2F | 3IF | 3F |
| Crabgrass | 1 | 5N | 2FC |
| Pigweed | 3FS | 4RSF | 3FS |
| | Example 51 | Example 29 | Example 34 |
| Tomato | 2F | 1 | 1 |
| Crabgrass | 3FS | 1 | 1 |
| Pigweed | 4FS | 1 | 1 |
| | Example 57 | Example 19 | Example 37 |
| Tomato | 3SF | 2F | 2F |
| Crabgrass | 4RS | 4RS | 4RS |
| Pigweed | 4SF | 4RS | 4RS |
| | Example 20 | Example 38 | Example 62 |
| Tomato | 4FS | 3F | 2F |
| Crabgrass | 5N | 4RS | 1 |
| Pigweed | 4RS | 4RS | 3FS |

PREEMERGENCE
1-5 SCALE
8 lb/a

| | Example 58 | Example 59 | Example 60 |
|---|---|---|---|
| Tomato | 2F | 3F | 1 |
| Crabgrass | 4RS | 5N | 2SC |
| Pigweed | 4SF | 4SF | 2S |
| | Example 61 | Example 63 | Example 64 |
| Tomato | 1 | 3F | 3F |
| Crabgrass | 1 | 1 | 4RS |
| Pigweed | 1 | 4FS | 4SF |
| | Example 65 | Example 66 | Example 68 |
| Tomato | 2F | 2F | 1 |
| Crabgrass | 4RS | 4RS | 1 |
| Pigweed | 4SF | 4SF | 2S |
| | Example 69 | | |
| Tomato | 1 | | |
| Crabgrass | 1 | | |
| Pigweed | 1 | | |
| | Example 44 | | |
| Tomato | 1 | | |
| Barnyard Grass | 1 | | |
| Mustard | 1 | | |
| Crabgrass | 1 | | |
| Pigweed | 1 | | |
| Velvetleaf | 3FS | | |
| Foxtail | 1 | | |
| Morningglory | 1 | | |
| Wildoat | 1 | | |

TABLE III-continued

| | |
|---|---|
| Zinnia | 1 |

Test II

The compound of Example 22 was tested on soybeans in the greenhouse. Soybeans were planted in 6-inch round pots, 1 plant per pot, and the test compound was sprayed over the foliage of the plants as a formulation substantially like those used in Test I above. A nonionic surfactant was added to each formulation at the rate of 0.5% of the total volume, which was 2 ml per plant. The compound was applied 35 days after the soybean seeds were planted, at the beginning of flowering, and the plants were observed 21 days after application. The following results were obtained.

In the table below, and in most of those which follow, numerical results such as height, number of pods, etc., are given in percent. Such results are always percentages based on the results observed in the untreated control plants.

TEST II

| Application Rate lb/A | No. of Pods/Plant % | Injury, 0-3 scale | Morphology 0-3 scale | Height % |
|---|---|---|---|---|
| 0.25 | 127 | 0.7 | 0.3 | 91 |
| 0.5 | 119 | 0.0 | 0.7 | 71 |
| 1.0 | 81 | 1.7 | 0.7 | 58 |
| Control | 100 | 0.0 | 0.0 | 100 |

Test III

The compound of Example 22 was tested substantially as described in Test II, except that the volume of formulation applied to each plant was 1 ml, containing 0.1% of added nonionic surfactant. The plants were treated 33 days after planting, at the beginning of flowering, and were observed 26 days after they were treated, with the following results.

TEST III

| Application Rate lb/A | No. of Pods/Plant % | Wt. of Pods/Plant % | Morphology 0-10 scale | Height % |
|---|---|---|---|---|
| 0.125 | 190 | 199 | 0.0 | 98 |
| 0.25 | 218 | 241 | 0.0 | 102 |
| 0.5 | 257 | 290 | 1.3 | 85 |
| 1.0 | 156 | 197 | 0.7 | 90 |
| Control | 100 | 100 | 0.0 | 100 |

Test IV

In this test, the compound of Example 22 was applied to soybean plants, 17 days after planting. The compound was formulated substantially as shown in Test I above, except that 0.1 of nonionic surfactant was added to each 2 ml portion of formulation to be applied to each plant. The plants were at the third trifoliate stage when the compound was applied. The plants were observed for epinasty 4 days after treatment, for injury and morphology 7 days after treatment, and for branching and height 14 days after treatment.

TEST IV

| Application Rate lb/A | Epinasty 0-3 scale | Injury 0-3 scale | Morphology 0-3 scale | Branching 0-3 scale | Height % |
|---|---|---|---|---|---|
| 0.25 | 0.0 | 0.0 | 1.0 | 1.7 | 44 |
| 0.5 | 0.3 | 0.0 | 1.0 | 1.3 | 31 |
| 1.0 | 0.3 | 0.0 | 1.3 | 2.7 | 19 |
| Control | 0.0 | 0.0 | 0.0 | 0.0 | 100 |

A number of compounds of the present invention were tested on soybeans, in the greenhouse, in a test carried out essentially as were those above. The compounds were formulated substantially as described in Test I, and 0.1% of a nonionic surfactant, based on the total volume, was added to each formulation. The volume of formulation applied to the foliage of each plant was 2 ml, applied 22 days after the soybean seeds had been planted.

The plants were observed for branching and for injury, both rated on a 0-10 scale, 13 days after treatment. On the twenty-fifth day after treatment, the plants were observed for the amount of growth in height, the total weight of the plants, the number of pods per plant, and the weight of the pods per plant. The results were as follows.

TEST V

| Ex. No. | Appln. Rate lb/A | Branching | Injury | Plant Wt. | No. Pods | Wt. Pods | Growth |
|---|---|---|---|---|---|---|---|
| Control | | 0.0 | 0.0 | 100% | 100% | 100% | 100% |
| 1 | 0.25 | 0.0 | 0.0 | 92 | 121 | 81 | 63 |
| | 0.125 | 0.0 | 0.0 | 101 | 148 | 82 | 39 |
| | 0.06 | 0.3 | 0.3 | 73 | 103 | 54 | 20 |
| 2 | 0.25 | 1.0 | 0.3 | 81 | 83 | 53 | 26 |
| | 0.125 | 1.0 | 0.0 | 71 | 62 | 46 | 11 |
| | 0.06 | 2.0 | 0.7 | 52 | 44 | 35 | 3 |
| 3 | 0.25 | 2.3 | 1.3 | 80 | 42 | 34 | 8 |
| | 0.125 | 0.7 | 0.3 | 72 | 44 | 40 | 10 |
| | 0.06 | 1.0 | 0.3 | 52 | 36 | 26 | 4 |
| 5 | 0.25 | 1.0 | 1.0 | 64 | 47 | 34 | 9 |
| | 0.125 | 2.0 | 0.7 | 62 | 41 | 31 | 4 |
| | 0.06 | 1.7 | 1.0 | 51 | 24 | 22 | 4 |
| 6 | 0.25 | 0.7 | 0.3 | 73 | 57 | 48 | 14 |
| | 0.125 | 2.0 | 1.7 | 57 | 50 | 40 | 6 |
| | 0.06 | 0.3 | 2.3 | 48 | 46 | 25 | 3 |
| 12 | 0.25 | 0.0 | 0.0 | 84 | 82 | 50 | 33 |
| | 0.125 | 1.7 | 0.3 | 63 | 53 | 39 | 8 |
| | 0.06 | 1.7 | 0.7 | 50 | 27 | 24 | 3 |
| 13 | 0.25 | 0.0 | 0.0 | 82 | 96 | 60 | 54 |
| | 0.125 | 0.0 | 0.0 | 72 | 70 | 44 | 42 |

TEST V-continued

| Ex. No. | Appln. Rate lb/A | Branching | Injury | Plant Wt. | No. Pods | Wt. Pods | Growth |
|---|---|---|---|---|---|---|---|
| | 0.06 | 0.7 | 0.0 | 95 | 118 | 65 | 27 |
| 17 | 0.25 | 0.0 | 0.0 | 83 | 85 | 45 | 40 |
| | 0.125 | 0.7 | 0.0 | 82 | 83 | 49 | 20 |
| | 0.06 | 1.7 | 0.7 | 52 | 39 | 30 | 3 |
| 23 | 0.25 | 0.0 | 0.3 | 97 | 114 | 66 | 44 |
| | 0.125 | 0.0 | 0.0 | 81 | 74 | 45 | 29 |
| | 0.06 | 2.0 | 1.3 | 61 | 44 | 37 | 3 |
| 24 | 0.25 | 1.0 | 0.3 | 94 | 86 | 57 | 27 |
| | 0.125 | 0.7 | 1.0 | 74 | 44 | 33 | 9 |
| | 0.06 | 0.0 | 0.7 | 43 | 29 | 20 | 4 |
| 25 | 0.25 | 1.3 | 1.3 | 71 | 53 | 35 | 8 |
| | 0.125 | 2.3 | 1.0 | 61 | 46 | 38 | 7 |
| | 0.06 | 2.0 | 1.0 | 57 | 36 | 29 | 5 |
| 27 | 0.25 | 0.0 | 0.0 | 92 | 110 | 57 | 47 |
| | 0.125 | 0.0 | 0.3 | 88 | 72 | 54 | 30 |
| | 0.06 | 0.7 | 1.0 | 72 | 44 | 32 | 13 |
| 28 | 0.25 | 1.3 | 1.7 | 74 | 78 | 53 | 13 |
| | 0.125 | 0.0 | 1.7 | 60 | 38 | 30 | 6 |
| | 0.06 | 1.7 | 2.3 | 50 | 39 | 28 | 4 |
| 43 | 0.25 | 0.7 | 1.7 | 54 | 46 | 30 | 8 |
| | 0.125 | 1.3 | 1.0 | 64 | 38 | 35 | 4 |
| | 0.06 | 1.3 | 1.3 | 50 | 32 | 24 | 4 |

Test VI

Further compounds of the invention were tested on soybeans in the greenhouse in a method substantially the same as that of Test V. The compounds were applied to the foliage of each plant as the plants entered the reproductive stage.

The plants were observed for leaf morphology and epinasty 28 days and 42 days after treatment. Those characteristics were evaluated on the 0–10 scale. The number of pods per plant and the amount of growth over the last 25 days was determined 42 days after treatment, and were reported as percents of the control plant values.

| Test VI | | | | | | | |
|---|---|---|---|---|---|---|---|
| | | Percent of Control | | Leaf | | | |
| Treatment | Rate (lb/a) | Growth | Pods/Plant | Morphology | | Epinasty | |
| | | | | Early | Late | Early | Late |
| 57 | 0.03 | 52 | 93 | 0 | 0.7 | 0 | 0 |
| | 0.06 | 25 | 88 | 0 | 1.7 | 0 | 1.0 |
| | 0.13 | 22 | 69 | 0.3 | 2.0 | 0.7 | 0.3 |
| 19 | 0.03 | 69 | 101 | 0 | 1.3 | 0 | 0 |
| | 0.06 | 35 | 88 | 0 | 1.3 | 0 | 0.3 |
| | 0.13 | 17 | 87 | 0.7 | 2.7 | 0.7 | 0.7 |
| 37 | 0.03 | 80 | 105 | 0 | 0 | 0 | 0 |
| | 0.06 | 58 | 97 | 0 | 0 | 0 | 0 |
| | 0.13 | 18 | 77 | 0 | 2.0 | 1.0 | 1.3 |
| 20 | 0.03 | 16 | 73 | 3.0 | 3.7 | 1.3 | 0.7 |
| | 0.06 | 15 | 58 | 2.7 | 4.0 | 3.3 | 2.3 |
| | 0.13 | 8 | 29 | 3.7 | 4.0 | 5.3 | 4.3 |
| 38 | 0.03 | 35 | 98 | 0 | 0.7 | 0 | 0.3 |
| | 0.06 | 23 | 84 | 0.7 | 1.7 | 0.7 | 0.7 |
| | 0.13 | 21 | 67 | 0.7 | 3.3 | 0 | 0 |
| 64 | 0.03 | 38 | 100 | 0 | 0.1 | 0 | 1.0 |
| | 0.06 | 10 | 73 | 1.0 | 2.3 | 1.3 | 1.3 |
| | 0.13 | 17 | 53 | 1.7 | 3.7 | 1.3 | 2.7 |

Test VII

Sweet corn was grown in the greenhouse, 1 plant per 6 inch round pot. Twelve days after the seeds had been planted, each pot was treated with 20 ml of an aqueous dispersion, prepared substantially as described in Test I above, of a compound of the present invention. The aqueous dispersion was poured evenly over the soil in each pot. Thirty-one days after treatment, the plants were observed for the extent of lodging, for the overall height of the plants, and for the percentage of each plant's tassel which was sterile or barren, as judged by the absence of flowerets from part of the tassel. The results were as follows.

| Test VII | | | | |
|---|---|---|---|---|
| Example Number | Appl'n Rate | Lodging 0–10 Scale | Height % | Tassel Sterility % |
| Control | | 0.0 | 100 | 0 |
| 2 | 0.5 | 0.0 | 105 | 10 |
| | 1.0 | 0.7 | 104 | 13 |
| | 2.0 | 0.7 | 110 | 38 |
| 3 | 0.5 | 0.0 | 103 | 0 |
| | 1.0 | 1.0 | 100 | 7 |
| | 2.0 | 3.0 | 95 | 48 |
| 5 | 0.5 | 0.0 | 106 | 48 |
| | 1.0 | 2.7 | 88 | 73 |
| | 2.0 | 2.7 | 73 | 68 |
| 6 | 0.5 | 1.0 | 85 | 15 |
| | 1.0 | 1.7 | 78 | 43 |
| | 2.0 | 1.7 | 65 | 71 |
| 12 | 0.5 | 1.0 | 89 | 32 |
| | 1.0 | 1.3 | 93 | 75 |
| | 2.0 | 1.0 | 64 | 91 |

Test VIII

Various compounds of the present invention were applied to the foliage of corn plants, 14 days after the seeds had been planted in 10 inch round pots in the greenhouse. The compounds were formulated essentially as described in Test I, with 0.1% by volume of added nonionic surfactant, and 2 ml of formulation was applied to each plant. The plants were grown in the greenhouse with normal watering, and were observed on the forty-ninth day after treatment with the following results.

| Test VIII | | | | |
|---|---|---|---|---|
| Example Number | Application Rate lb/A | Height % | Tassel Emergence % | Tassel Sterility % |
| Control | | 100 | 100 | 17 |

-continued

| | | Test VIII | | |
|---|---|---|---|---|
| Example Number | Application Rate lb/A | Height % | Tassel Emergence % | Tassel Sterility % |
| 2 | 0.5 | 103 | 100 | 73 |
| | 1.0 | 108 | 100 | 67 |
| | 2.0 | 78 | 100 | 96 |
| 3 | 0.5 | 108 | 100 | 7 |
| | 1.0 | 107 | 100 | 17 |
| | 2.0 | 115 | 100 | 3 |
| 5 | 0.5 | 91 | 100 | 60 |
| | 1.0 | 98 | 100 | 70 |
| | 2.0 | 74 | 67 | 47 |
| 6 | 0.5 | 86 | 100 | 73 |
| | 1.0 | 88 | 100 | 67 |
| | 2.0 | 49 | 67 | 100 |
| 12 | 0.5 | 62 | 100 | 100 |
| | 1.0 | 34 | 33 | 100 |
| | 2.0 | 29 | 0 | 100 |

Test IX

Sweet corn was grown in the field, and the plots, each consisting of a 10 foot length of 1 row, were identified. The compound of Example 1, formulated as a 1 lb/gal aqueous suspension, and the compound of Example 22, formulated as a 50% wettable powder, were applied to the corn, at the volume rate of 100 ml per plot, applied as a fine spray to the foliage. Optimum-population plots, having about 25,500 plants per acre, and high-population plots, having about 37,000 plants per acre, were used. Three treatment dates were used, 25 days, 42 days and 57 days after the seed had been planted. The corn was allowed to grow out to full maturity, and it was then harvested. The table reports the yield of the various plots, based on 15.5% moisture in the grain.

| | | Test IX | | |
|---|---|---|---|---|
| Example Number | Application Rate lb/A | Application Date | Population | Yield % |
| Control | | | | 100 |
| 1 | 0.5 | Early | Low | 80 |
| | 1.0 | | | 92 |
| | 2.0 | | | 91 |
| | 0.5 | | High | 81 |
| | 1.0 | | | 90 |
| | 2.0 | | | 90 |
| | 0.5 | Middle | Low | 103 |
| | 1.0 | | | 96 |
| | 2.0 | | | 95 |
| | 0.5 | | High | 96 |
| | 1.0 | | | 89 |
| | 2.0 | | | 75 |
| | 0.5 | Late | Low | 88 |
| | 1.0 | | | 88 |
| | 2.0 | | | 84 |
| | 0.5 | | High | 102 |
| | 1.0 | | | 115 |
| | 2.0 | | | 101 |
| 2 | 0.5 | Early | Low | 88 |
| | 1.0 | | | 95 |
| | 2.0 | | | 92 |
| | 0.5 | | High | 90 |
| | 1.0 | | | 112 |
| | 2.0 | | | 88 |
| | 0.5 | Middle | Low | 94 |
| | 1.0 | | | 80 |
| | 2.0 | | | 70 |
| | 0.5 | | High | 97 |
| | 1.0 | | | 77 |
| | 2.0 | | | 63 |
| | 0.5 | Late | Low | 97 |
| | 1.0 | | | 101 |
| | 2.0 | | | 96 |
| | 0.5 | | High | 97 |
| | 1.0 | | | 87 |
| | 2.0 | | | 98 |

Test X

Cotton plants were grown in the greenhouse in 6 inch round pots, and the foliage of the plants was sprayed 40 days after the seeds had been planted with formulations of certain compounds of the invention. The formulations were prepared essentially as described in Test I, and 0.1%, based on the total volume, of a nonionic surfactant was added to the formulations before spraying. Two ml of surfactant was sprayed over the foliage of each plant. The plants were returned to the greenhouse after treatment, and were given appropriate care. After 27 days, plants were observed and changes in morphology were rated on the 0–10 scale. The amount of growth that the plants had achieved was also noted. After 40 days, the number of squares and bolls on the plants were counted. The results were as follows.

| | | Test X | | |
|---|---|---|---|---|
| Example Number | Application Rate lb/A | Morphology | Growth % | Squares & Bolls % |
| Control | | 0.0 | 100 | 100 |
| 1 | 0.125 | 0.0 | 92 | 85 |
| | 0.25 | 0.0 | 104 | 128 |
| | 0.5 | 0.0 | 98 | 128 |
| 2 | 0.125 | 0.0 | 105 | 123 |
| | 0.25 | 0.0 | 98 | 101 |
| | 0.5 | 0.0 | 82 | 117 |
| 3 | 0.125 | 0.0 | 101 | 107 |
| | 0.25 | 0.0 | 94 | 85 |
| | 0.5 | 0.3 | 64 | 155 |
| 5 | 0.125 | 0.0 | 63 | 133 |
| | 0.25 | 1.3 | 27 | 139 |
| | 0.5 | 2.7 | 24 | 59 |
| 6 | 0.125 | 0.0 | 98 | 128 |
| | 0.25 | 0.0 | 83 | 160 |
| | 0.5 | 0.0 | 58 | 139 |
| 12 | 0.125 | 0.0 | 100 | 85 |
| | 0.25 | 0.0 | 93 | 91 |
| | 0.5 | 0.0 | 105 | 117 |

Test XI

In this test, cotton plants grown in the greenhouse were treated with the compounds of Example 1 and 22 of the present invention as foliar applications, formulated essentially as described in Test I. The plants were treated at the 5-leaf stage, 24 days after the seeds had been planted. They were observed for injury, 9 days after treatment; for changes in morphology, 17 days after treatment; and for height, branching and morphology, 32 days after treatment. The following observations were made. Injury, morphology and branching were rated on the 0–10 scale.

| | Test XI | |
|---|---|---|
| Example | Application | Morphology |

-continued

| Test XI | | | |
|---|---|---|---|
| Number | Rate | Injury | 17 days |
| 1 | 0.25 | 0.0 | 0.7 |
|  | 0.5 | 0.3 | 3.3 |
|  | 1.0 | 1.0 | 4.0 |
| 22 | 0.5 | 0.0 | 0.0 |
|  | 1.0 | 0.0 | 0.7 |
|  | 2.0 | 0.0 | 3.3 |
| Control |  | 0.0 | 0.0 |

| Example Number | Application Rate | Morphology 32 days | Branching | Height % |
|---|---|---|---|---|
| 1 | 0.25 | 1.3 | 7.3 | 93 |
|  | 0.5 | 5.0 | 5.7 | 92 |
|  | 1.0 | 5.7 | 5.3 | 73 |
| 22 | 0.5 | 0.0 | 7.3 | 103 |
|  | 1.0 | 1.0 | 6.3 | 96 |
|  | 2.0 | 2.3 | 6.7 | 82 |
| Control |  | 1.3 | 4.3 | 100 |

Test XII

Field-grown cotton was treated with the compounds of Examples 1 and 22, both formulated as 1 lb/gal aqueous suspensions. The plants were treated at 3 different stages, the square stage, the early flowering stage and the green boll stage. The plants were observed 84 days after the first treatments were made, when the height was measured and a rating of leaf morphology was made on the 0-10 scale. Each experimental unit was 10 feet of 1 row, and 3 replicates made up each treatment group. The results were as follows.

| Test XII | | | | |
|---|---|---|---|---|
| Example Number | Application Rate | Treatment | Morphology | Height % |
| 1 | 0.25 | Early | 1.7 | 83 |
|  | 0.5 |  | 3.3 | 67 |
|  | 1.0 |  | 4.3 | 69 |
|  | 2.0 |  | 7.7 | 58 |
|  | 0.25 | Middle | 3.3 | 94 |
|  | 0.5 |  | 3.3 | 94 |
|  | 1.0 |  | 2.3 | 85 |
|  | 2.0 |  | 2.3 | 76 |
|  | 0.25 | Late | 1.0 | 92 |
|  | 0.5 |  | 0.0 | 90 |
|  | 1.0 |  | 0.0 | 99 |
|  | 2.0 |  | 0.0 | 88 |
| 22 | 0.25 | Early | 1.7 | 83 |
|  | 0.5 |  | 3.0 | 76 |
|  | 1.0 |  | 6.0 | 61 |
|  | 2.0 |  | 7.7 | 58 |
|  | 0.25 | Middle | 0.7 | 90 |
|  | 0.5 |  | 0.7 | 90 |
|  | 1.0 |  | 2.0 | 78 |
|  | 2.0 |  | 2.3 | 69 |
|  | 0.25 | Late | 0.0 | 92 |
|  | 0.5 |  | 0.0 | 92 |
|  | 1.0 |  | 0.0 | 90 |
|  | 2.0 |  | 0.7 | 87 |
| Control |  |  | 0.0 | 100 |

Test XIII

Sugar beets were grown in the greenhouse, and were treated at the 4-leaf stage with the compound of Example 22. Formulations substantially like those of Test I were used, and 1 ml of formulation was sprayed on the foliage of each plant. The plants were cared for in the greenhouse for 41 days after treatment, and were then evaluated. Morphology was rated on the 0-10 scale, the leaves and root were weighed, the number of leaves was counted, and the total area of the leaves was determined. The results were as follows.

| | Test XIII | | | |
|---|---|---|---|---|
| Application Rate lb/a | Morphology | Number Leaves % | Area Leaves % | Weight Leaves % | Weight Root % |
| Control | 0.0 | 100 | 100 | 100 | 100 |
| 0.25 | 4.0 | 103 | 89 | 100 | 96 |
| 0.5 | 5.5 | 108 | 84 | 106 | 87 |
| 1.0 | 7.0 | 91 | 71 | 92 | 95 |

Test XIV

In this test, greenhouse-grown sugar beet plants were treated with the compound of Example 22 at the 8-9 leaf stage. The compound was formulated substantially like the formulations of Test I, and 1.5 ml of formulation was sprayed over the foliage of each plant. The plants were cared for in the greenhouse for 54 days, and were then evaluated for injury, on the 0-10 scale, for the area and weight of the leaves, and for the weight of the root. The results were as follows.

Test XIV

| | Test XIV | | | |
|---|---|---|---|---|
| Application Rate lb/a | Injury | Weight Leaves % | Area Leaves % | Weight Root % |
| Control | 0.0 | 100 | 100 | 100 |
| 0.25 | 3.7 | 79 | 73 | 106 |
| 0.5 | 6.7 | 100 | 76 | 82 |
| 1.0 | 8.7 | 63 | 53 | 68 |

Test XV

Kentucky Bluegrass and Pennfine ryegrass were grown in 4 inch square pots in the greenhouse. the grass was well established, about 15 days old, it was clipped short, and was then sprayed with formulations of a number of compounds of the present invention. One ml of formulation, substantially like those of Test I, was applied to each pot. After 15 days, the grass was evaluated for injury, on the 0-10 scale, and after 22 days, it was evaluated for growth inhibition, also on the 0-10 scale. The results were as follows.

| | | Test XV | | | |
|---|---|---|---|---|---|
| Example Number | Application Rate lb/A | Ryegrass | | Bluegrass | |
| | | Injury | Growth Inhibition | Injury | Growth Inhibition |
| Control |  | 0.0 | 0.0 | 0.0 | 0.0 |
| 2 | 0.25 | 0.0 | 0.7 | 0.0 | 1.0 |
|  | 0.5 | 0.0 | 0.0 | 0.0 | 0.0 |
|  | 1.0 | 0.0 | 1.7 | 0.0 | 3.0 |
| 3 | 0.25 | 0.0 | 0.0 | 0.0 | 0.0 |
|  | 0.5 | 0.0 | 0.0 | 0.0 | 0.3 |
|  | 1.0 | 0.0 | 0.0 | 0.0 | 0.0 |
| 5 | 0.25 | 0.0 | 0.3 | 0.0 | 1.0 |
|  | 0.5 | 0.0 | 1.3 | 0.0 | 1.3 |
|  | 1.0 | 0.0 | 2.0 | 0.0 | 2.3 |
| 12 | 0.25 | 0.0 | 0.0 | 0.0 | 0.0 |
|  | 0.5 | 0.0 | 0.3 | 0.0 | 1.0 |
|  | 1.0 | 0.0 | 3.3 | 0.0 | 3.0 |
| 23 | 0.25 | 0.0 | 0.0 | 0.0 | 1.0 |
|  | 0.5 | 0.0 | 0.7 | 0.0 | 3.0 |
|  | 1.0 | 0.0 | 0.0 | 0.0 | 2.3 |
| 24 | 0.25 | 0.0 | 0.0 | 0.0 | 0.0 |
|  | 0.5 | 0.0 | 1.7 | 0.0 | 1.7 |

Test XV (continued)

| Example Number | Application Rate lb/A | Ryegrass Injury | Ryegrass Growth Inhibition | Bluegrass Injury | Bluegrass Growth Inhibition |
|---|---|---|---|---|---|
| | 1.0 | 0.0 | 0.3 | 0.0 | 2.7 |
| 25 | 0.25 | 0.0 | 3.3 | 0.0 | 3.3 |
| | 0.5 | 0.0 | 0.0 | 0.0 | 0.3 |
| | 1.0 | 0.0 | 0.3 | 0.0 | 1.0 |
| 27 | 0.25 | 0.0 | 0.0 | 0.0 | 0.3 |
| | 0.5 | 0.0 | 2.7 | 0.0 | 2.3 |
| | 1.0 | 0.0 | 1.0 | 0.0 | 3.0 |
| 39 | 0.25 | 0.0 | 0.0 | 0.0 | 1.0 |
| | 0.5 | 0.0 | 1.0 | 0.0 | 1.3 |
| | 1.0 | 2.7 | 3.3 | 2.7 | 3.3 |
| 40 | 0.25 | 0.0 | 0.0 | 0.0 | 0.0 |
| | 0.5 | 0.0 | 2.3 | 0.0 | 3.0 |
| | 1.0 | 0.0 | 3.7 | 1.0 | 4.0 |

Test XVI

In this test, several compounds were tested on green foxtail grown in 4 inch square pots in the greenhouse. The grass was grown and the compounds were formulated and applied as described in Test XV above. The grass was cared for in the greenhouse for 22 days, and then it was evaluated for inhibition of seedhead formation, on the 0-0 scale, and the fresh weight of the plants was determined. The following results were obtained.

| Example Number | Application Rate | Seedhead Inhibition | Plant Weight % |
|---|---|---|---|
| Control | | 0.0 | 100 |
| 2 | 0.25 | 4.3 | 69 |
| | 0.5 | 6.0 | 72 |
| | 1.0 | 10.0 | 21 |
| 3 | 0.25 | 0.0 | 100 |
| | 0.5 | 0.0 | 99 |
| | 1.0 | 3.7 | 114 |
| 5 | 0.25 | 2.7 | 93 |
| | 0.5 | 10.0 | 35 |
| | 1.0 | 5.0 | 61 |
| 6 | 0.25 | 9.0 | 50 |
| | 0.5 | 10.0 | 50 |
| | 1.0 | 10.0 | 54 |
| 12 | 0.25 | 1.0 | 116 |
| | 0.5 | 3.7 | 77 |
| | 1.0 | 9.0 | 46 |

Test XVII

Waldren wheat was grown in 4 inch square pots in the greenhouse, and was treated with the compounds of Examples 1 and 22 when the wheat was in the boot stage. The compounds were formulated substantially as described in Test I, and the formulations were sprayed over the foliage of the plants. The wheat was grown in the greenhouse with ordinary care for 44 days, and then was evaluated by making a number of measurements on the main stems and on the tillers of the plants. The results were as follows.

| Example Number | Application Rate lb/a | No. Stems % | Height Stems % | No. Tillers % | Height Tillers % |
|---|---|---|---|---|---|
| Control | | 100 | 100 | 100 | 100 |
| 1 | 1.5 | 102 | 100 | 98 | 88 |
| | 3.0 | 102 | 104 | 98 | 90 |
| 22 | 1.5 | 107 | 100 | 102 | 95 |
| | 3.0 | 102 | 102 | 112 | 93 |

| Example Number | Application Rate lb/a | Weight Tiller Heads % | Weight Heads % |
|---|---|---|---|
| Control | | 100 | 100 |
| 1 | 1.5 | 117 | 101 |
| | 3.0 | 90 | 97 |
| 22 | 1.5 | 93 | 90 |
| | 3.0 | 99 | 104 |

Test XVIII

A number of compounds of the present invention were foliar-applied to wheat, growing in 4 inch square pots, when the plants were at the 4-5 leaf, 1-2 tiller stage. The compounds were formulated substantially as described in Test I, and 2 ml of formulation was applied to the plants in each pot. The plants were cared for in the greenhouse for 56 days, and then the average plant height was determined. Seventy days after the treatments were applied, the seedheads were evaluated for injury on the 0-10 scale. The following results were observed.

| Example Number | Application Rate lb/a | Height % | Head Injury |
|---|---|---|---|
| Control | | 100 | 0.4 |
| 1 | 0.06 | 101 | 1.0 |
| | 0.12 | 103 | 0.0 |
| | 0.25 | 104 | 0.0 |
| 4 | 0.06 | 93 | 0.7 |
| | 0.12 | 99 | 1.0 |
| | 0.25 | 98 | 0.0 |
| 7 | 0.06 | 102 | 0.0 |
| | 0.12 | 101 | 0.0 |
| | 0.25 | 102 | 0.0 |
| 8 | 0.06 | 92 | 0.7 |
| | 0.12 | 91 | 1.3 |
| | 0.25 | 96 | 1.0 |
| 9 | 0.06 | 93 | 0.3 |
| | 0.12 | 99 | 0.0 |
| | 0.25 | 96 | 1.3 |
| 26 | 0.06 | 101 | 0.0 |
| | 0.12 | 102 | 0.0 |
| | 0.25 | 90 | 1.3 |
| 28 | 0.06 | 95 | 2.0 |
| | 0.12 | 98 | 2.0 |
| | 0.25 | 91 | 2.7 |
| 29 | 0.06 | 100 | 0.3 |
| | 0.12 | 97 | 0.0 |
| | 0.25 | 103 | 0.7 |
| 41 | 0.06 | 99 | 0.3 |
| | 0.12 | 100 | 0.0 |
| | 0.25 | 102 | 1.0 |
| 42 | 0.06 | 92 | 3.0 |
| | 0.12 | 89 | 3.0 |
| | 0.25 | 81 | 2.0 |
| 43 | 0.06 | 87 | 2.0 |
| | 0.12 | 87 | 2.7 |
| | 0.25 | 95 | 4.0 |
| 55 | 0.06 | 106 | 0.7 |
| | 0.12 | 99 | 0.0 |
| | 0.25 | 103 | 1.3 |
| 56 | 0.06 | 104 | 0.3 |
| | 0.12 | 98 | 1.0 |
| | 0.25 | 112 | 0.0 |

Test XIX

This test was carried out substantially as was Test XVIII, except that the observations of injury to the seedheads and plant height were made 41 days after the treatments were applied.

| Example Number | Test XIX Application Rate lb/a | Height % | Head Injury |
|---|---|---|---|
| Control |  | 100 | 0.0 |
| 2 | 0.06 | 95 | 0.0 |
|  | 0.12 | 92 | 2.3 |
|  | 0.25 | 80 | 4.3 |
| 3 | 0.06 | 86 | 2.7 |
|  | 0.12 | 83 | 5.3 |
|  | 0.25 | 65 | 6.3 |
| 5 | 0.06 | 98 | 0.7 |
|  | 0.12 | 96 | 0.7 |
|  | 0.25 | 87 | 4.7 |
| 12 | 0.06 | 89 | 1.0 |
|  | 0.12 | 90 | 4.0 |
|  | 0.25 | 84 | 4.0 |
| 23 | 0.06 | 92 | 1.7 |
|  | 0.12 | 90 | 3.0 |
|  | 0.25 | 79 | 5.0 |
| 24 | 0.06 | 98 | 1.7 |
|  | 0.12 | 81 | 3.0 |
|  | 0.25 | 82 | 3.7 |
| 25 | 0.06 | 106 | 0.7 |
|  | 0.12 | 95 | 2.0 |
|  | 0.25 | 86 | 3.0 |
| 39 | 0.06 | 100 | 0.0 |
|  | 0.12 | 90 | 2.7 |
|  | 0.25 | 83 | 5.3 |
| 40 | 0.06 | 91 | 0.7 |
|  | 0.12 | 89 | 1.0 |
|  | 0.25 | 88 | 3.3 |

Test XX

Waldren wheat, growing in 4 inch square pots, was treated with compounds of the invention when it was at the 4-leaf 0-tiller stage. The compounds were formulated substantially as described in Test I, and 2 ml of formulation was applied to the plants in each pot. The plants were cared for in the greenhouse for 50 days, and then the average height of the plants was measured. After 64 days, injury to the seedheads was rated on the 0–10 scale. The following results were observed.

| Example Number | Test XX Application Rate lb/a | Height % | Head Injury |
|---|---|---|---|
| Control |  | 100 | 0.4 |
| 1 | 0.06 | 91 | 0.0 |
|  | 0.12 | 94 | 0.7 |
|  | 0.25 | 95 | 0.7 |
| 10 | 0.06 | 96 | 0.3 |
|  | 0.12 | 91 | 0.7 |
|  | 0.25 | 95 | 0.0 |
| 11 | 0.06 | 102 | 1.3 |
|  | 0.12 | 104 | 0.0 |
|  | 0.25 | 97 | 0.0 |
| 16 | 0.06 | 98 | 0.7 |
|  | 0.12 | 106 | 0.3 |
|  | 0.25 | 108 | 0.3 |
| 17 | 0.5 | 95 | 1.7 |
|  | 1.0 | 89 | 3.7 |
|  | 2.0 | 91 | 2.7 |
| 30 | 0.06 | 92 | 0.3 |
|  | 0.12 | 96 | 1.0 |
|  | 0.25 | 101 | 0.7 |
| 36 | 0.5 | 95 | 2.3 |
|  | 1.0 | 101 | 2.7 |
|  | 2.0 | 97 | 3.3 |

Test XXI

In this test, both wheat and barley plants were treated, the barley at the 4-leaf stage and the wheat at the 3-leaf stage. The foliage of the plants, growing in 4-inch square pots, was sprayed with formulations prepared substantially as described in Test I, of which 1.5 ml was applied to the plants in each pot. After 36 days of growth in the greenhouse, the wheat was evaluated for the number of stems with heads, for morphology of the heads, and for height, and the barley was evaluated after 56 days for the number of tillers present in the treated plants. The results were as follows.

| | | | Test XXI | Wheat | | |
|---|---|---|---|---|---|---|
| Example Number | Application Rate lb/A | Barley Number Tillers | Number Stems w/Heads | Head Morphology | Height % |
| Control |  | 100% | 100% | 0.0 | 100 |
| 2 | 0.25 | 82 | 136 | 3.0 | 72 |
|  | 0.5 | 106 | 76 | 4.3 | 67 |
|  | 1.0 | 84 | 15 | 1.3 | 40 |
| 3 | 0.25 | 97 | 152 | 3.7 | 79 |
|  | 0.5 | 91 | 106 | 4.7 | 56 |
|  | 1.0 | 95 | 30 | 4.0 | 62 |
| 5 | 0.25 | 95 | 106 | 4.0 | 58 |
|  | 0.5 | 95 | 106 | 3.0 | 55 |
|  | 1.0 | 100 | 61 | 3.7 | 46 |
| 12 | 0.25 | 82 | 121 | 3.7 | 67 |
|  | 0.5 | 104 | 91 | 4.0 | 60 |
|  | 1.0 | 88 | 15 | 1.7 | 44 |
| 23 | 0.25 | 108 | 197 | 3.7 | 73 |
|  | 0.5 | 104 | 121 | 4.3 | 61 |
|  | 1.0 | 73 | 15 | 2.0 | 47 |
| 24 | 0.25 | 93 | 106 | 3.0 | 62 |
|  | 0.5 | 95 | 76 | 2.0 | 66 |
|  | 1.0 | 88 | 15 | 1.3 | 39 |
| 25 | 0.25 | 93 | 152 | 5.3 | 72 |
|  | 0.5 | 93 | 30 | 2.0 | 74 |
|  | 1.0 | 91 | 30 | 3.3 | 48 |
| 27 | 0.25 | 95 | 136 | 4.0 | 75 |
|  | 0.5 | 104 | 136 | 5.0 | 63 |
|  | 1.0 | 128 | 121 | 4.0 | 70 |
| 39 | 0.25 | 91 | 121 | 2.7 | 86 |
|  | 0.5 | 91 | 91 | 4.0 | 50 |
|  | 1.0 | 91 | 45 | 3.7 | 46 |
| 40 | 0.25 | 102 | 167 | 3.7 | 77 |
|  | 0.5 | 95 | 152 | 3.3 | 57 |
|  | 1.0 | 102 | 15 | 1.3 | 52 |

Text XXII

Rice plants were grown in 1 quart metal cans in the greenhouse, and were treated with the compounds of Examples 1 and 22. The compounds were formulated substantially as described in Test I. Some plants were treated 18 days after planting, with 2 ml of formulation sprayed over the foliage. Other plants were treated 32 days after planting, with 50 ml of formulation poured over the soil in which the plants grew. The plants were cared for in the greenhouse, and were observed 69 days after the soil-drench applications, with the following results.

| Test XXII | | | | | | |
|---|---|---|---|---|---|---|
| Example Number | Application Rate lb/A | Treatment | No. Tillers % | No. Heads % | Wt. Heads % | Wt. Foliage % |
| Control | | | 100 | 100 | 100 | 100 |
| 1 | 0.5 | Foliar | 116 | 106 | 106 | 105 |
| | 1.0 | | 137 | 106 | 96 | 108 |
| | 2.0 | | 100 | 91 | 78 | 97 |
| 22 | 0.5 | | 147 | 126 | 108 | 101 |
| | 1.0 | | 95 | 91 | 97 | 101 |
| | 2.0 | | 137 | 91 | 92 | 102 |
| 1 | 0.5 | Soil | 136 | 114 | 109 | 107 |
| | 1.0 | | 123 | 119 | 99 | 106 |
| | 2.0 | | 101 | 85 | 73 | 94 |
| 22 | 0.5 | | 110 | 97 | 94 | 101 |
| | 1.0 | | 102 | 102 | 95 | 92 |
| | 2.0 | | 118 | 97 | 72 | 105 |

Test XXIII

McIntosh apple seedlings were treated with compounds of the present invention, 28 days after the seeds were planted. The compounds were formulated substantially as described in Test I, and 25 ml of formulation was applied to the soil around each seedling. The seedlings were cared for in the greenhouse for 28 days after treatment, and their growth was then measured. The results were as follows.

| Test XXIII | | |
|---|---|---|
| Example Number | Application Rate lb/A | Growth % |
| Control | | 100 |
| 1 | 0.12 | 99 |
| | 0.25 | 127 |
| | 0.5 | 72 |
| 2 | 0.12 | 114 |
| | 0.25 | 107 |
| | 0.5 | 142 |
| 3 | 0.12 | 115 |
| | 0.25 | 108 |
| | 0.5 | 136 |
| 5 | 0.12 | 98 |
| | 0.25 | 90 |
| | 0.5 | 71 |
| 6 | 0.12 | 79 |
| | 0.25 | 65 |
| | 0.5 | 125 |
| 12 | 0.12 | 55 |
| | 0.25 | 108 |
| | 0.5 | 104 |

Test XXIV

The compound of Example 22 was applied as a soil drench to silver maple trees in 6 inch round pots. The compound was formulated by dissolving 6 mg of it in 0.6 ml of dimethylsulfoxide, and diluting the solution to 150 ml for 3 replicate trees at 1 lb/A. The higher treatment rate was formulated in the same way, with 25 mg of compound. The trees were cared for in the greenhouse for 27 days, and were then evaluated for injury on the 0–3 scale, and for stem length. The injury at 1 and 4 lb/A as 0.3 and 0.0, respectively, and the stem length was 116% and 83% of controls, respectively.

Test XXV

Four compounds of the invention were tested on Williams soybeans in field plots in the midwestern United States. The soybeans were planted in 38-inch rows, 8–10 seeds/ft, and each plot consisted of 25 feet of two rows. The compounds were formulated as 1 lb/gal aqueous suspensions, the formulae of which are given below in the compositions section. The compositions were diluted with water and applied in a volume of 50 gal/A in all cases, to the foliage of the plants. Two application times were used, the V3 stage, 33 days after planting, and the R1–R2 stage, 55 days after planting. About 3 months after planting, the mid-season height and width of the plants were measured, and injury and leaf morphology were rated on the 0–10 scale. When the plants were mature, the yield of the plots was determined.

| Example Number | Rate lb/A | Height % | Width % | Injury | Morphology | Yield % |
|---|---|---|---|---|---|---|
| Test XXV-V3 | | | | | | |
| Control | | 100 | 100 | 0 | 0 | 100 |
| 1 | .016 | 99 | 101 | 0 | 0 | 102 |
| | .032 | 99 | 100 | 0 | 0.1 | 101 |
| | .063 | 99 | 98 | 0 | 0.1 | 101 |
| | .125 | 99 | 100 | 0 | 0 | 100 |
| 3 | .016 | 98 | 92 | 0 | 0.6 | 100 |
| | .032 | 98 | 88 | 0 | 1.0 | 100 |
| | .063 | 96 | 92 | 0 | 1.8 | 96 |
| | .125 | 88 | 84 | 0 | 2.0 | 95 |
| 5 | .016 | 98 | 98 | 0 | 0.4 | 101 |
| | .032 | 94 | 94 | 0 | 0.9 | 101 |
| | .063 | 98 | 90 | 0 | 1.2 | 103 |
| | .125 | 86 | 80 | 0 | 2.0 | 92 |
| 6 | .016 | 97 | 101 | 0 | 1.2 | 100 |
| | .032 | 96 | 95 | 0 | 1.5 | 100 |
| | .063 | 91 | 84 | 0 | 1.8 | 90 |
| | .125 | 81 | 81 | 0 | 2.2 | 86 |
| Test XXV R1–R2 | | | | | | |
| Control | | 100 | 100 | 0 | 0 | 100 |
| 1 | .016 | 99 | 98 | 0 | 0 | 104 |
| | .032 | 96 | 94 | 0 | 0.4 | 101 |
| | .063 | 98 | 95 | 0 | 0.6 | 102 |
| | .125 | 96 | 98 | 0 | 0.5 | 98 |
| 3 | .016 | 99 | 98 | 0 | 0.1 | 101 |
| | .032 | 93 | 90 | 0 | 0.9 | 97 |
| | .063 | 82 | 80 | 0 | 1.8 | 90 |
| | .125 | 78 | 77 | 0 | 1.5 | 80 |
| 5 | .016 | 98 | 98 | 0 | 0.1 | 97 |
| | .032 | 93 | 88 | 0 | 1.2 | 91 |
| | .063 | 80 | 68 | 0 | 2.0 | 84 |
| | .125 | 72 | 64 | 0 | 1.8 | 66 |
| | .016 | 99 | 101 | 0 | 0 | 100 |
| | .032 | 92 | 95 | 0 | 0.8 | 94 |
| | .063 | 82 | 77 | 0 | 1.5 | 87 |
| | .125 | 72 | 63 | 0 | 2.0 | 72 |

Test XXVI

Deltapine 41 cotton was grown in the southern United States for tests with four compounds of the invention. Each plant was treated separately and evaluated separately, and each treatment group consisted of three plants. The compounds were supplied as 1 lb/gal aqueous suspensions, the formulae of which are given below. The proper amounts of the compositions were diluted and sprayed evenly over the foliage of the plants.

Some plants were treated at the early flower stage, and some when they had 5–15 mature bolls. Thirty days after treating, the plants were observed for injury, rated on the 0–10 scale. Injury was expressed as necrosis and/or reduction in the number of squares and bolls. Forty days after treating, growth inhibition was rated on the 0-10 scale. Sixty days after treating, the plants were rated for injury, growth inhibition, the number of bolls/plant, and boll malformation on the 0-10 scale.

TABLE XXVI

| Example Number | Appl'n Rate lb/A | Injury 30 days | Injury 60 days | Growth 40 days | Growth 60 days | Bolls/ Plant, % | Malformed Bolls |
|---|---|---|---|---|---|---|---|
| Flower stage | | | | | | | |
| Control | | 0.0 | 0.0 | 0.0 | 0.0 | 100 | 0.0 |
| 1 | 0.25 | | 0.0 | 0.0 | 0.0 | 82 | 6.7 |
|  | 0.5 | | 3.7 | 1.0 | 1.0 | 68 | 7.0 |
|  | 1.0 | | 5.3 | 1.0 | 1.0 | 53 | 7.7 |
| 3 | 0.25 | | 6.0 | 0.7 | 0.3 | 35 | 8.0 |
|  | 0.5 | | 7.0 | 1.7 | 2.0 | 35 | 7.0 |
|  | 1.0 | | 9.2 | 5.0 | 5.3 | 6 | 7.7 |
| 5 | 0.25 | | 8.7 | 4.7 | 4.3 | 11 | 8.0 |
|  | 0.5 | | 9.3 | 3.3 | 4.0 | 5 | 9.0 |
|  | 1.0 | | 9.5 | 4.3 | 5.3 | 3 | 9.8 |
| 6 | 0.25 | | 3.0 | 1.8 | 1.7 | 36 | 5.0 |
|  | 0.5 | | 7.0 | 3.3 | 2.3 | 21 | 6.3 |
|  | 1.0 | | 8.7 | 4.0 | 3.0 | 10 | 8.7 |
| Boll stage | | | | | | | |
| 1 | 0.25 | 0.0 | 0.0 | 0.0 | 0.0 | 70 | 0.0 |
|  | 0.5 | 0.0 | 0.0 | 0.0 | 0.0 | 85 | 0.3 |
|  | 1.0 | 0.5 | 2.7 | 0.0 | 0.0 | 53 | 1.7 |
| 3 | 0.25 | 0.0 | 1.3 | 0.0 | 0.0 | 87 | 0.7 |
|  | 0.5 | 0.0 | 2.3 | 0.0 | 0.0 | 70 | 2.3 |
|  | 1.0 | 0.0 | 6.3 | 0.7 | 0.0 | 34 | 5.0 |
| 5 | 0.06 | 0.0 | 2.7 | 0.0 | 0.0 | 76 | 2.7 |
|  | 0.12 | 1.7 | 6.0 | 0.0 | 0.0 | 40 | 5.7 |
|  | 0.25 | 1.7 | 4.3 | 0.0 | 0.0 | 47 | 4.7 |
| 6 | 0.25 | 0.0 | 2.3 | 0.0 | 0.0 | 84 | 1.7 |
|  | 0.5 | 0.0 | 4.0 | 0.0 | 0.0 | 56 | 3.7 |
|  | 1.0 | 1.0 | 5.3 | 0.0 | 0.0 | 70 | 5.7 |

Text XXVII

Cotton plants were grown in the greenhouse and tested substantially as described in Test X. The plants were treated when they were in the square stage. The number of bolls and of flowers and squares was counted 34 days after treatment and reported as percent of the control values. The amount of growth was also measured at 34 days and reported as percent of the growth of the control plants, and leaf morphology was assessed at the same time.

TABLE XXVII

| Example Number | Application Rate lb/a | No. of Flowers & Squares | No. of Bolls | Leaf Morphology | Growth |
|---|---|---|---|---|---|
| 57 | 0.06 | 89% | 91% | 0.0 | 64% |
|  | 0.12 | 136 | 122 | 0.0 | 52 |
|  | 0.25 | 76 | 152 | 0.0 | 47 |
| 38 | 0.06 | 119 | 61 | 0.3 | 87 |
|  | 0.12 | 119 | 61 | 0.0 | 73 |
|  | 0.25 | 59 | 81 | 0.0 | 47 |

TABLE XXVII-continued

| Example Number | Application Rate lb/a | No. of Flowers & Squares | No. of Bolls | Leaf Morphology | Growth |
|---|---|---|---|---|---|
| Control | | 100 | 100 | 0.0 | 100 |

Test XXVIII

Compounds were tested against 8 typical species of plants in a method that was essentially the same as Method B in Test I above, except that the application rate was 4 lb/A, rather than 8 lb/A.

In this test the following abbreviations are used.

| SYBN | Soybean | MNGY | Morning Glory |
| BRLY | Barley | FTMI | Foxtail Millet |
| MSTD | Mustard | TMTO | Tomato |
| LACG | Large Crabgrass | RRPW | Red Root Pigweed |

TABLE XXVIII

| EX. NO. | SYBN | BRLY | MSTD | LACG | MNGY | FTMI | TMTO | RRPW |
|---|---|---|---|---|---|---|---|---|
| Preemergence | | | | | | | | |
| 72 | 4RS | 2SF | 4SF | 3SF | 2F | 4RS | 4FS | 4SF |
| 73 | 4RS | 3SF | 4SF | 4SF | 3SF | 3SF | 4SF | |
| 74 | 4RSF | 3SF | 4RSF | 2SF | 2SF | 3RSF | 3RSF | 4RSF |
| 75 | 4RSF | 3SF | 4RSF | 4RSF | 1 | 4RSF | 2SF | 4RSF |
| Postemergence | | | | | | | | |
| 72 | 4SFZ | 3FS | 4SF | 3SF | 3SF | 3SF | 4SF | 4SF |
| 73 | 3SFZ | 3SF | 4SF | 2F | 3SF | 3SF | 4SF | 4SF |
| 74 | 4FSZ | 3FS | 4FS | 2FS | 2FS | 3FS | 4FS | 4FS |
| 75 | 3FSZ | 2FS | 4FS | 2FS | 3FS | 3FS | 3FS | 3FS |

Test XXIX

Four compounds of the invention were applied to spring barley in field plots in the midwestern United States. The compounds were applied over the foliage in the form of water dispersions prepared from a 1 lb/gal aqueous suspension. Applications were made at 4 different times, as follows:
- (A) Stage 2–4, leaf sheaths beginning to lengthen, plants beginning to tiller to beginning of the erection of the pseudo-stem
- (B) Stage 6–7, first and second node visible, next to last leaf visible
- (C) Stage 7–8, second node formed, last leaf rolled but visible, ear beginning to swell
- (D) Stage 9–10, ligule of last leaf visible to sheath of last leaf grown out, ear swollen but not visible Lodging and growth inhibition were rated at harvest time, and crop injury was rated about two weeks after treatment. No injury was observed from any treatment. Lodging is reported on a 0–10 scale, where 0 indicates no lodging, and growth inhibition is in percent. Yield is corrected to a standard moisture content.

TABLE XXIX

Stage A

| Cpd. of Ex. No. | Appl'n Rate lb/A | Lodging | Yield bu/A | % Moisture | Wt. of 1000 Seed g | % Growth Inhib. |
|---|---|---|---|---|---|---|
| 2 | 0.06 | 3.5 | 73.5 | 10.1 | 35.3 | 7 |
|  | 0.12 | 5.0 | 68.7 | 10.5 | 35.6 | 7 |
|  | 0.25 | 3.8 | 64.7 | 10.6 | 35.8 | 9 |
|  | 0.50 | 3.8 | 77.3 | 10.5 | 36.0 | 9 |
| 5 | 0.06 | 4.8 | 67.6 | 10.4 | 35.9 | 7 |
|  | 0.12 | 5.5 | 76.3 | 10.3 | 36.4 | 4 |
|  | 0.25 | 4.0 | 78.2 | 10.3 | 36.4 | 10 |
|  | 0.50 | 4.0 | 72.5 | 10.5 | 36.0 | 9 |
| 6 | 0.06 | 2.8 | 77.6 | 10.0 | 36.0 | 9 |
|  | 0.12 | 1.3 | 67.1 | 10.8 | 36.3 | 11 |
|  | 0.25 | 0.8 | 56.8 | 10.3 | 35.8 | 18 |
|  | 0.50 | 0 | 46.3 | 9.6 | 35.4 | 21 |
| 12 | 0.06 | 3.8 | 82.1 | 10.0 | 36.0 | 7 |
|  | 0.12 | 3.0 | 73.5 | 10.0 | 35.3 | 13 |
|  | 0.25 | 1.4 | 60.1 | 10.4 | 35.5 | 34 |
|  | 0.50 | 0.1 | 42.7 | 10.6 | 35.7 | 20 |
| Control |  | 5.8 | 75.4 | 10.2 | 35.9 | 0 |

Stage B

| Cpd. of Ex. No. | Appl'n Rate lb/A | Lodging | Yield bu/A | % Moisture | Wt. of 1000 Seed g | % Growth Inhib. |
|---|---|---|---|---|---|---|
| 2 | 0.06 | 5.3 | 82.1 | 10.4 | 35.7 | 7 |
|  | 0.12 | 4.8 | 72.5 | 10.4 | 35.4 | 8 |
|  | 0.25 | 5.8 | 74.4 | 10.7 | 35.4 | 7 |
|  | 0.50 | 4.5 | 73.5 | 10.3 | 35.5 | 11 |
| 5 | 0.06 | 6.0 | 76.0 | 10.4 | 35.8 | 7 |
|  | 0.12 | 4.8 | 78.2 | 9.6 | 35.8 | 8 |
|  | 0.25 | 3.8 | 68.7 | 10.3 | 35.3 | 15 |
|  | 0.50 | 3.0 | 77.3 | 9.9 | 35.5 | 10 |
| 6 | 0.06 | 2.0 | 72.5 | 10.2 | 35.9 | 11 |
|  | 0.12 | 1.3 | 83.0 | 10.1 | 35.8 | 14 |
|  | 0.25 | 0.8 | 68.7 | 10.5 | 35.9 | 19 |
|  | 0.50 | 0.1 | 53.4 | 10.4 | 35.7 | 22 |
| 12 | 0.06 | 1.5 | 69.7 | 10.2 | 35.2 | 13 |
|  | 0.12 | 1.8 | 71.6 | 10.0 | 35.1 | 16 |
|  | 0.25 | 0.8 | 52.5 | 10.3 | 35.2 | 21 |
|  | 0.50 | 0 | 21.0 | 10.2 | 35.4 | 25 |
| Control |  | 6.3 | 77.3 | 10.0 | 36.2 | 0 |

Stage C

| Cpd. of Ex. No. | Appl'n Rate lb/A | Lodging | Yield bu/A | % Moisture | % Growth Inhib. |
|---|---|---|---|---|---|
| 2 | 0.06 | 4.5 | 64.9 | 10.3 | 5 |
|  | 0.12 | 4.5 | 59.2 | 10.6 | 8 |
|  | 0.25 | 4.0 | 72.5 | 9.7 | 5 |
|  | 0.50 | 3.8 | 69.7 | 9.8 | 4 |
| 5 | 0.06 | 4.0 | 64.9 | 10.4 | 1 |
|  | 0.12 | 4.3 | 73.5 | 9.7 | 0 |
|  | 0.25 | 3.8 | 72.5 | 10.1 | 2 |
|  | 0.50 | 4.0 | 73.5 | 10.3 | 2 |
| 6 | 0.06 | 2.8 | 58.2 | 10.6 | 4 |
|  | 0.12 | 2.2 | 59.2 | 10.6 | 6 |

TABLE XXIX-continued

|  | 0.25 | 1.0 | 65.8 | 10.3 | 11 |
|---|---|---|---|---|---|
|  | 0.50 | 0.5 | 53.4 | 10.2 | 19 |
| 12 | 0.06 | 2.8 | 68.7 | 10.2 | 5 |
|  | 0.12 | 2.5 | 66.8 | 10.5 | 7 |
|  | 0.25 | 2.0 | 73.9 | 10.1 | 11 |
|  | 0.50 | 0.6 | 57.3 | 10.4 | 15 |
| Control |  | 5.6 | 67.7 | 10.3 | 0 |

Stage D

| Cpd. of Ex. No | Appl'n Rate lb/A | Lodging | Yield bu/A | % Moisture | % Growth Inhib. |
|---|---|---|---|---|---|
| 2 | 0.06 | 4.0 | 78.7 | 9.5 | 7 |
|  | 0.12 | 2.8 | 73.0 | 9.3 | 7 |
|  | 0.25 | 2.8 | 75.4 | 9.6 | 7 |
|  | 0.50 | 2.0 | 72.5 | 9.6 | 10 |
| 5 | 0.06 | 3.8 | 75.4 | 9.5 | 7 |
|  | 0.12 | 2.0 | 69.7 | 9.3 | 7 |
|  | 0.25 | 3.0 | 82.1 | 9.6 | 6 |
|  | 0.50 | 2.1 | 78.2 | 9.4 | 7 |
| 6 | 0.06 | 2.0 | 75.4 | 9.8 | 10 |
|  | 0.12 | 2.3 | 67.7 | 9.5 | 8 |
|  | 0.25 | 2.8 | 86.4 | 9.3 | 9 |
|  | 0.50 | 1.0 | 62.0 | 9.7 | 15 |
| 12 | 0.06 | 2.8 | 71.1 | 10.3 | 7 |
|  | 0.12 | 3.0 | 74.2 | 9.7 | 11 |
|  | 0.25 | 1.0 | 60.6 | 9.9 | 12 |
|  | 0.50 | 0.5 | 56.8 | 9.7 | 13 |
| Control |  | 6.7 | 85.9 | 9.4 | 0 |

Test XXX

A test was carried out on Auburn winter wheat in field plots, according to the general plan of Test XXIX. The compounds were applied in the spring, at the following growth stages.
- (A) Stage 4, plants tillering, erection of pseudo stem, leaf sheaths beginning to lengthen
- (B) Stage 7, second node formed, next to last leaf visible
- (C) Stage 9–10, last leaf just visible to completely grown out, ear swollen but not visible
- (D) Stage 10.1–10.3, ears just visible to one-half of heading process complete The same parameters were measured as in Test XXIX. Again, there was no crop injury. Lodging was not observed in the control or any treatment. Fertilizer application to the field was not uniform, and some variability of the results seems to have resulted.

TABLE XXX

| Cpd. of Ex. No. | Appl'n Rate lb/A | Yield bu/A | % Moisture | Wt. of 1000 Seeds g | % Growth Inhib. |
|---|---|---|---|---|---|
| Stage A |  |  |  |  |  |
| 2 | 0.06 | 38.9 | 16.2 | 22.6 | +2 |
|  | 0.12 | 34.0 | 14.9 | 22.8 | 5 |
|  | 0.25 | 30.5 | 14.7 | 25.2 | 13 |
|  | 0.50 | 33.2 | 12.0 | 27.9 | 2 |
| 5 | 0.06 | 34.7 | 15.2 | 22.2 | 5 |
|  | 0.12 | 45.3 | 14.0 | 24.5 | 2 |
|  | 0.25 | 35.0 | 14.6 | 27.1 | 7 |
|  | 0.50 | 17.2 | 14.6 | 23.9 | 13 |
| 6 | 0.06 | 28.1 | 17.3 | 22.9 | 9 |
|  | 0.12 | 28.6 | 17.6 | 23.8 | 10 |
|  | 0.25 | 27.5 | 15.7 | 24.7 | 11 |
|  | 0.50 | 22.9 | 13.9 | 25.8 | 10 |
| 12 | 0.06 | 31.1 | 16.0 | 20.5 | 3 |
|  | 0.12 | 33.4 | 14.2 | 23.0 | 3 |
|  | 0.25 | 32.4 | 16.1 | 25.5 | 4 |
|  | 0.50 | 12.1 | 14.2 | 26.7 | 9 |
| Control |  | 35.9 | 15.2 | 21.9 | 0 |
| Stage B |  |  |  |  |  |
| 2 | 0.06 | 47.3 | 12.9 | 23.2 | +5 |

TABLE XXX-continued

| Cpd. of Ex. No. | Appl'n Rate lb/A | Yield bu/A | % Moisture | Wt. of 1000 Seeds g | % Growth Inhib. |
|---|---|---|---|---|---|
|   | 0.12 | 42.4 | 13.4 | 24.4 | 3 |
|   | 0.25 | 38.0 | 12.5 | 24.3 | 7 |
|   | 0.50 | 36.9 | 12.7 | 23.7 | +2 |
| 5 | 0.06 | 41.8 | 12.8 | 22.4 | 5 |
|   | 0.12 | 43.4 | 12.8 | 23.5 | 3 |
|   | 0.25 | 39.5 | 12.2 | 23.0 | 5 |
|   | 0.50 | 36.5 | 13.1 | 24.5 | 4 |
| 6 | 0.06 | 41.5 | 12.9 | 24.9 | 3 |
|   | 0.12 | 38.9 | 14.0 | 24.2 | 2 |
|   | 0.25 | 39.7 | 13.5 | 24.3 | 6 |
|   | 0.50 | 38.5 | 13.4 | 22.9 | 3 |
| 12 | 0.06 | 45.3 | 13.2 | 23.5 | 0 |
|   | 0.12 | 45.5 | 12.7 | 24.2 | 1 |
|   | 0.25 | 30.9 | 13.7 | 26.1 | 8 |
|   | 0.50 | 35.1 | 12.6 | 25.8 | 3 |
| Control |   | 42.7 | 13.1 | 22.2 | 0 |
| Stage C |   |   |   |   |   |
| 2 | 0.06 | 48.9 | 10.8 | 22.4 | 3 |
|   | 0.12 | 44.1 | 10.6 | 21.8 | 6 |
|   | 0.25 | 43.9 | 10.4 | 22.0 | 10 |
|   | 0.50 | 45.4 | 10.6 | 21.2 | 5 |
| 5 | 0.06 | 47.7 | 12.3 | 22.8 | 3 |
|   | 0.12 | 46.9 | 11.2 | 22.9 | 0 |
|   | 0.25 | 46.6 | 9.9 | 22.1 | 7 |
|   | 0.50 | 44.1 | 10.4 | 21.2 | 6 |
| 6 | 0.06 | 35.3 | 12.7 | 23.4 | 9 |
|   | 0.12 | 34.0 | 12.6 | 23.0 | 9 |
|   | 0.25 | 45.8 | 11.3 | 23.1 | 9 |
|   | 0.50 | 42.0 | 11.0 | 23.0 | 11 |
| 12 | 0.06 | 47.2 | 11.6 | 22.8 | 2 |
|   | 0.12 | 40.8 | 11.1 | 21.8 | 3 |
|   | 0.25 | 41.8 | 11.4 | 21.7 | 4 |
|   | 0.50 | 38.5 | 12.0 | 21.6 | 10 |
| Control |   | 46.8 | 12.1 | 22.8 | 0 |
| Stage D |   |   |   |   |   |
| 2 | 0.06 | 55.2 | 9.5 | 23.7 | 3 |
|   | 0.12 | 74.0 | 8.3 | 23.3 | 5 |
|   | 0.25 | 55.1 | 10.5 | 23.3 | 6 |
|   | 0.50 | 71.6 | 9.0 | 23.1 | 1 |
| 5 | 0.06 | 60.7 | 10.3 | 23.7 | 1 |
|   | 0.12 | 64.9 | 9.4 | 23.7 | 2 |
|   | 0.25 | 59.7 | 9.7 | 24.1 | 4 |
|   | 0.50 | 75.0 | 8.1 | 23.8 | 3 |
| 6 | 0.06 | 52.1 | 10.0 | 24.2 | 8 |
|   | 0.12 | 64.0 | 9.3 | 24.6 | 8 |
|   | 0.25 | 53.4 | 11.0 | 24.5 | 7 |
|   | 0.50 | 55.9 | 9.3 | 24.7 | 6 |
| 12 | 0.06 | 61.3 | 8.9 | 23.4 | 4 |
|   | 0.12 | 57.5 | 9.4 | 23.2 | 3 |
|   | 0.25 | 65.7 | 9.1 | 23.7 | 4 |
|   | 0.50 | 50.2 | 10.0 | 24.3 | 8 |
| Control |   | 59.9 | 10.4 | 23.9 | 0 |

Methods of Use

The tests above demonstrate that the compounds of the present invention have a variety of regulatory effects on the growth habits of numerous species of plants. Perhaps the most important effect of the compounds is their ability to slow the growth and decrease the size of plants. Thus, the treated plants occupy less space and can be planted more densely. The treated plants are shorter and stronger, and therefore less likely to be lodged by wind and rain. In general, the smaller plant will have a reduced need for nutrients, as well.

The plants also exhibit effects on the pollen-producing and seed-producing organs of plants, particularly of monocotyledons such as grasses, wheat, rice, corn and the like, but also on dicotyledons such as cotton and the like. Thus, when a compound of the invention is applied to a turf grass, the formation of seed heads as well as the growth of the grass is inhibited. The appearance of the turf is greatly improved thereby. Further, and of more economic importance, is the gametocidal effect of the compounds. Application of a compound to a plant will inhibit or prevent the plants' production of pollen. Thus, the non-pollenating plant can be easily used as the female parent in plant hybridization. For example, the compounds can beneficially be used as gametocides in producing hybrid corn, wheat, rice and the like.

Further, the compounds increase branching, flowering, and the number of pods set on various crop plants, particularly on soybeans. As a result, the yield per plant is increased over untreated plants. Since it may well be possible to plant more closely when a compound of the invention is to be used, the possibility of significant yield benefits is offered.

Still further, the compounds confer other growth effects. Depending on the species of plant of concern, the application rate, the time of application and perhaps other factors as well, effects such as reduced internodal length, increased number of nodes, an increase in the number of nodes which bear a leaf, a branch or a flower, improvement in the plant's or an individual leaf's morphology, or improvements in the structure and extent of the treated plant's root system, are provided by compounds of the invention.

The soybean is a particularly preferred plant for use of the present compounds. A group of preferred plants includes soybean, dry bean and other beans grown for human consumption, alfalfa, cotton and peanut. Another group of preferred plants includes turf grasses, corn, wheat, barley, rice, rye and oats. Still another group of preferred plants includes fruit trees, ornamental trees and nut trees. A group of more highly preferred plants for use of the present compounds includes soybean, sugar beet, cotton and corn. Wheat and barley make up another highly preferred group.

The time and manner of applying a compound of the present invention to a plant may be varied. It appears to be preferable to apply it before or near the beginning of the plant's reproductive stage. The compounds may be beneficially applied, however, up to the late reproductive stage of the plant.

It is preferred to apply the compound directly to the plant, or to the soil in which the plant is rooted, as the plant nears the stage at which it is to be treated. It is most preferred to apply the compound as a foliar spray directly to the plant. It is conventional to formulate agriculturally useful compounds as water-dispersed formulations for such applications, and the use of such compositions is preferred in the practice of the present invention.

It may be more beneficial to apply a compound two or more times at relatively short intervals. Plants in a field do not all develop at the same time, even though they were all planted at once. Therefore, an application which is perfectly timed for the slower-developing plants may be too late for the earlier ones. Applying a compound twice, or even three or four times, at intervals of a few or several days will improve its performance, and therefore the performance of the treated crop, under some circumstances.

The data reported above show that many of the compounds are active at extremely low application rates. A preferred range of application rates is from about 0.015 to about 0.5 lb/A. Another preferred range of rates, particularly for use on soybeans, is from about 0.06 to about 0.25 lb/A. From about 0.03 to about 0.25 lb/A is another preferred rate range. Still another preferred range, particularly for the less active compounds, is from about 0.25 to about 2 lb/A. However, rates in the broad range from about 0.015 to about 5 lb/A are used in particular instances, particularly when the maximum degree of size reduction, or other regulatory effect, is called for.

Compositions

Formulated compositions of the compounds of the present invention constitute an important aspect of the invention. Such compositions comprise a compound of the invention and a phytologically-acceptable diluent. The most economical and preferred compositions are concentrated water-emulsifiable or water-dispersable compositions. Such compositions include, in general, emulsifiable concentrates, suspension concentrates, wettable powders and wettable granules, all of which are commonly used in the agricultural chemical art. Some discussion of them will be provided, however, to assure understanding by the reader.

The concentration of a compound in a concentrated composition is entirely irrelevant to the use of the compound. Such compositions are diluted in water for application, and the application rate of the compound is determined by the ratio at which the composition is diluted in water, or by the amount of the composition which is applied per area of crop land. Thus, any desired application rate can be obtained from any concentrated composition. Farmers and agricultural chemists are acquainted with the simple calculations which are necessary.

Emulsifiable concentrates of the compounds comprise a convenient concentration of the compound dissolved in a phytologically-acceptable diluent which is a mixture of water-immiscible organic solvent and emulsifiers. Useful organic solvents, in general, include aromatics, especially xylenes, and the petroleum fractions, especially the naphthalenic and olefinic portions of petroleum, such as those called heavy aromatic naphthas. Terpenic solvents including rosin derivatives, and complex alcohols such as 2-ethoxyethanol are also often used, and amides such as dimethylacetamide may be particularly useful with the present compounds. Suitable emulsifiers for emulsifiable concentrates, generally used in amounts in the range of from about 1% to about 10% by weight of the concentrate, are frequently found among the alkylbenzenesulfonates, the alkyl sulfates, the non-ionics such as ethylene oxide adducts of alkylphenol, and especially among the metal and amine salts of alkyl sulfates.

Wettable powders comprise an intimate mixture of the compound and a phytologically-acceptable diluent made up of an inert carrier and surfactants. The inert carrier is usually chosen from among easily water-dispersable powdery substances such as attapulgite clay, the montmorillonite clays, the diatomaceous earths and the purified silicates. Surfactants for wettable powders are found among the same types just mentioned for emulsifiable concentrates, as well as the sulfonated lignins and the naphthalenesulfonates. It is possible to compact a wettable powder into granular form, and thereby to produce a wettable granule, which has the advantage of being non-dusty and easy to measure and pour. When added to water, a properly formulated wettable granular product will disperse and become a fine suspension.

The compounds may also be formulated as suspensions, which consist of a relatively high concentration, in the interest of economy, of the compound in finely powdered form, dispersed and suspended in a phytologically-acceptable aqueous diluent. A surfactant system for a suspension product is much like that used in a wettable powder, but it must be capable of maintaining the compound in dispersed form over a long period of time. It is sometimes advisable to adjust the density of the liquid, as by dissolving an inert salt in it, in order to assist in the suspension of the relatively dense particles of compound.

When an aqueous dispersion of a compound, prepared by the dilution of a concentrated composition, is to be applied to foliage, an adjuvant is often used to improve the ability of the dispersion to wet and adhere to the foliage. Such adjuvants as vegetable gums, emulsified polybutenes, cationic and other surfactants and lignin derivatives are often used. The use of an adjuvant in aqueous dispersions of the present compounds is highly preferred, and regularly improves results. Not only the commercial adjuvants, which are commonly known to growers, but also ordinary surfactants, are beneficially used, at concentrations in the range of a few tenths of a percent in the dispersion.

Aqueous dispersions of concentrated compositions may be applied either to foliage or to the soil in which the plants grow. When the application is to be to the soil, a granular composition can also be effectively used. A granular agricultural composition consists of the compound, applied, usually in a relatively low concentration such as from about 0.1% to about 10% by weight, to a granular carrier having a convenient particle size for application. Typically, the particle size range is from 20 to 60 mesh, on the standard U.S. sieve size scale. Such carriers as clay, sand, pulverized stone, corncob grits and the like are frequently used and may be chosen for convenience and economy. It is usually unnecessary to use any adjuvant or other ingredient other than the compound and the carrier, with perhaps a small amount of solvent in which the compound is applied to the carrier. The carrier may also be supplied in powdered form, and formulated by mixing the powdered carrier with the powdered compound and then compacting the mixture and granulating it to the desired particle size range.

The following examples of compositions of compounds of the present invention are given, to assure that agricultural chemists understand the manner in which the compounds are formulated.

| Suspension of Example 1 | |
| --- | --- |
| Compound of Example 1 | 12.5% |
| Tergitol TMN-6 (non-ionic surfactant) | 10.0 |
| Purified silica | 1.0 |
| Polyfon H (lignin sulfonate salt) | 0.5 |
| 2% xanthan gum | 10.0 |
| Silicone antifoam | 0.2 |
| Water | 65.8 |

The compound was ground with the silica, the Polyfon and part of the water in an attrition mill until 50% of the particles were smaller than 2.3 microns. The milled suspension was then mixed with the rest of the ingredients.

| Wettable Powder of Example 22 | |
|---|---|
| Compound of Example 22 | 52.1% |
| Polyfon O (lignin sulfonate salt) | 5.0 |
| Purified silica | 5.0 |
| Sodium lauryl sulfate | 5.0 |
| Kaolin clay | 32.9 |

The ingredients were mixed and milled twice through an air impact mill, so that 50% of the particles were smaller than 4.2 microns.

| Suspension of Example 22 | |
|---|---|
| Compound of Example 22 | 12.5% |
| Purified silica | 1.0 |
| Polyfon H | 0.5 |
| Silicone antifoam | 0.2 |
| Tergitol TMN-6 | 10.0 |
| 2% xanthan gum | 10.0 |
| Water | 65.8 |

The compound was milled with the Tergitol, the anitfoam, the silica, the Polyfon and part of the water in an attrition mill until 50% of the particles were smaller than 2 microns. It was then mixed with the xanthan and the rest of the water.

| Suspension of Example 5 | |
|---|---|
| Compound of Example 5 | 12.5% |
| Silicone antifoam | 0.2 |
| Purified silica | 1.0 |
| 2% xanthan gum | 10.0 |
| Nonionic surfactant | 10.0 |
| Water | 66.3 |

The product was processed as was the suspension immediately above.

| Emulsifiable Concentrate of Example 1 | |
|---|---|
| Compound of Example 1 | 6.2% |
| Propylene glycol methyl ether | 20.0 |
| Heavy aromatic naphtha | 70.6 |
| Toximul H (anionic surfactant) | 1.6 |
| Toximul D (anionic surfactant) | 1.6 |

| Suspension of Example 3 | |
|---|---|
| Compound of Example 3 | 12.5% |
| Inert ingredients as used in Suspension of Example 5 | 87.5 |

The product was processed as was the Suspension of Example 5, milling to a particle size range where 50% of the particles were smaller than 2.2 microns.

| Suspension of Example 6 | |
|---|---|
| Compound of Example 6 | 12.5% |
| Inert ingredients as used in Suspension of Example 5 | 87.5 |

The product was processed as was the Suspension of Example 5, milling to a particle size range where 50% of the particles were smaller than 1.9 microns.

| Emulsifiable Concentrate of Example 1 | |
|---|---|
| Compound of Example 1 | 6.2% |
| Propylene glycol methyl ether | 20.0 |
| Heavy aromatic naptha | 68.0 |
| Toximul H | 2.9 |
| Toximul D | 2.9 |

We claim:

1. A compound of the formula wherein
n is 0, 1 or 2;
X is —O— or —S—;
the R groups independently are halo, trifluoromethyl, trifluoromethoxy, difluoromethoxy, pentafluoroethoxy, 1,1,2,2-tetrafluoroethoxy, $C_1$–$C_3$ alkyl or $C_1$–$C_3$ alkoxy;
$R^1$ is $C_1$–$C_4$ primary or secondary alkyl;
$R^2$ is hydroxy, $C_1$–$C_4$ alkoxy, benzyloxy, phenoxy, —N($R^4$)($R^5$) or a moiety forming a phytologically-acceptable salt;
$R^3$ is hydrogen or $C_1$–$C_4$ primary or secondary alkyl;
$R^4$ and $R^5$ independently are hydrogen, $C_3$–$C_6$ cycloalkyl or $C_1$–$C_3$ alkyl, or $R^4$ and $R^5$ combine with the nitrogen atom to which they are attached to form morpholino, pyrrolidino or piperidino.

2. A compound of claim 1 wherein $R^1$ is methyl.
3. A compound of claim 1 wherein $R^3$ is hydrogen.
4. A compound of claim 1 wherein R is halo or trifluoromethyl and n is 1 or 2.
5. A compound of claim 1 wherein X is —O—.
6. The compound of claim 1 which is 3-(1-carboxyethoxy)-1-(3,4-dichlorophenyl)-1,2,4-1H-triazole or a phytologically-acceptable salt thereof.
7. The compound of claim 1 which is 1-(3,4-dichlorophenyl)-3-(1-ethoxycarbonylethoxy)-1,2,4-1H-triazole.
8. The compound of claim 1 which is 1-(3-chlorophenyl)-3-(1-ethoxycarbonylethoxy)-1,2,4-1H-triazole.
9. The compound of claim 1 which is 3-(1-carboxyethoxy) -3-(1-ethoxycarbonylethoxy)-1,2,4-1H-triazole or a phytologically-acceptable salt thereof.
10. The compound of claim 1 which is 3-(1-carboxyethoxy)-1-(4-chlorophenyl)-1,2,4-1H-triazole or a phytologically-acceptable salt thereof.
11. The compound of claim 1 which is 1-(4-chlorophenyl)-3-(1-ethoxycarbonylethoxy)-1,2,4-1H-triazole.
12. The compound of claim 1 which is 3-(1-ethoxycarbonylethoxy)-1-(3-trifluoromethylphenyl)-1,2, 4-1H-triazole.
13. The compound of claim 1 which is 3-(1-carboxyethoxy)-1-(3-trifluoromethylphenyl)-1,2,4-1H-triazole or a phytologically-acceptable salt thereof.
14. A compound of claim 1 in combination with a phytologically-acceptable diluent.
15. A combination of claim 14 wherein the compound is a compound wherein $R^1$ is methyl and X is —O—.
16. A combination of claim 14 wherein the compound is a compound wherein $R^3$ is hydrogen.

17. A combination of claim 14 wherein the compound is a compound wherein R is halo or trifluoromethyl and n is 1 or 2.

18. A combination of claim 17 wherein the compound is a compound wherein $R^1$ is methyl and $R^3$ is hydrogen.

19. A method of regulating the growth of plants which comprises applying an effective amount of a compound of claim 1 to a plant at a time not later than the late reproductive growth stage.

20. A method of claim 19 wherein the compound is a compound wherein $R^1$ is methyl.

21. A method of claim 19 wherein the compound is a compound wherein $R^3$ is hydrogen.

22. A method of claim 19 wherein the compound is a compound wherein R is halo or trifluoromethyl and n is 1 or 2.

23. A method of claim 22 wherein the compound is a compound wherein $R^1$ is methyl and $R^3$ is hydrogen.

24. The compound of claim 1 which is 3-(1-carboethoxy)-1-(3,5-dichlorophenyl)-1, 2,41H-triazle or a phytologically-acceptable salt thereof.

25. The compound of claim 1 which is 1-(3,5-dichlorophenyl)-3-(1-ethoxycarbonylethoxy)-1,2,4-1H-triazole.

26. A method for improving the yield of a soybean plate which comprises applying an effective amount of a compound of claim 1 to the plant at a time not later than the late reproductive growth stage.

* * * * *

UNITED STATES PATENT AND TRADEMARK OFFICE
CERTIFICATE OF CORRECTION

PATENT NO. : 4,931,083

DATED : June 5, 1990

INVENTOR(S) : James R. Beck and Richard K. Mann

It is certified that error appears in the above—identified patent and that said Letters Patent is hereby corrected as shown below:

Column 20, lines 8-9 please delete "1-(4-bromophenyl)-3-(1-pyrrolidinocarbonylethoxy)-1,2,4-1H-triazole" and insert -- 1-(4-bromophenyl)-3-(1-propylaminocarbonylethoxy)-1,2,4-1H-triazole --.

Column 20, lines 40-41 please delete "1-(3-bromophenyl)-3-(1-pyrrolidinocarbonylethoxy)-1,2,4-1H-triazole" and insert -- 1-(3-bromophenyl)-3-(1-propylaminocarbonylethoxy)-1,2,4-1H-triazole --.

Column 31, line 34 please delete "Example 6" and insert -- Example 56 --.

Column 46, line 49 please add -- 6 -- in the column headed "Control" before ".016  99  101  0  0  100".

Signed and Sealed this

Nineteenth Day of November, 1991

Attest:

HARRY F. MANBECK, JR.

Attesting Officer

Commissioner of Patents and Trademarks